(12) United States Patent
Wyler et al.

(10) Patent No.: US 6,214,968 B1
(45) Date of Patent: *Apr. 10, 2001

(54) FIBROBLAST STIMULATING GROWTH FACTOR 1 (FSF-1) AND THE EARLY DETECTION OF FIBROSIS

(75) Inventors: David J. Wyler, Newton; Sadhana Prakash, Cambridge; Xiaoping Zhang, Malden, all of MA (US)

(73) Assignee: New England Medical Center Hospitals, Inc., Boston, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/465,343

(22) Filed: Jun. 5, 1995

Related U.S. Application Data

(60) Division of application No. 08/395,674, filed on Feb. 28, 1995, now abandoned, which is a continuation-in-part of application No. 08/152,904, filed on Nov. 15, 1993, now abandoned, which is a continuation of application No. 07/840,426, filed on Feb. 24, 1992, now abandoned.

(51) Int. Cl.[7] .............................. C07K 14/00; C07K 14/52

(52) U.S. Cl. .................... 530/300; 530/350; 530/351; 435/69.1; 435/69.5; 514/2; 424/85.1

(58) Field of Search .................................. 530/350, 331, 530/300; 435/69.1, 69.5; 514/2; 424/85.1

(56) References Cited

FOREIGN PATENT DOCUMENTS

WO 93/16715    9/1993 (WO).

OTHER PUBLICATIONS

Sporn et al. 1988. Peptide growth factors are multifunctional. Nature, vol. 332, pp. 217–219, Mar. 1988.*
Baird et al. 1986. Inhbibition of endothelial cell proliferation by type–beta transforming growth factor: interactions with acidic and basic fibroblast growth factors. Biochem. Biophys. Res. Commun. vol. 138, pp. 476–482, Jul. 1986.*
Roberts et al. 1986. Transforming growth factor type–beta: rapid induction of fibrosis and angiogenesis in vivo and stimulation of collagen formation in vitro. Proc. Natl. Acad. Sci. USA, vol. 83, pp. 4167–4171, Jun. 1986.*
Shipley et al. 1986. Reversible inhition of normal human prokeratinocyte proliferation by type beta transforming growth factor–gorwth inhibitor is serum–free medium. Cancer Res., vol. 46, pp. 2068–2071, Apr. 1986.*
Beck et al. 1990. Accelerated healing of ulcer wounds in the rabbit ear by recombinant human transforming grrowth–beta 1. Growth Factors, vol. 2, pp. 273–282, Feb. 1990.*
Hebda et al. 1988. Stimulatory effects of transforming growth factor –beta and epidermal growth factor on epidermal cell outgrowth from porcine skin expalnt cultures. J. Invest. Dermatol., vol. 91, pp. 440–445, Nov. 1988.*
Bowie et al. 1990. Deciphering the message in protein sequences: tolerance to amino acid substitutions. Science, vol. 247, 1306–1310, Mar. 1990.*
George et al, "Current methods in sequence comparison and analysis," in Macromolecular Sequencing and Synthesis, Selected Methods and Applications, 1988, D.H. Schlesinger (ed.), Alan R. Liss, Inc., New York, NY, pp. 127–149, 1988.*
Barton, "Protein sequence alignment and database scanning," in Protein Structure Prediction, A Practical Approach, 1996 IRL Press at Oxford University Press, Oxford, UK, pp. 31–63, 1996.*
Aebersold et al., "Internal amino acid sequence analysis of proteins separated by one– or two–dimensional gel electrophoresis . . . " Proc. Nat'l. Acad. Sci. USA 84:6970–6874, 1987.
Creighton, T., "Proteins: Structures and Molecular Principles" by W.H. Freeman and Company, pp. 93–131, published 1983.
Bowie et al., "Deciphering the message in protein sequences: Tolerance to amino acid substitutions" Science 247:1306–1310, 1990.
Miller et al., "Gene transfer and antisense nucleic acid techniques" Parasitology Today 19(3):92–97, 1994.
Gospodarowicz et al., "Purification of the Fibroblast Growth Factor Activity from Bovine Brain", 1978, *J. Biological Chem.*, 253(10):3736–43.*
Harper et al., "Human Class 1 Heparin–Binding Growth Factor: Structure and Homology to Bovine Acidic Brain Fibroblast Growth Factor," 1986, *American Chemical Society*, 25:4097–4103.*
LeGendre et al., "Direct Protein Microsequencing from Immobilon™ –P Transfer Membrane", 1988, *Biotechniques*, 6:154–59.*
Lobb et al., "Purification of Heparin–Binding Growth Factors," 1986, *Analytical Biochemistry* , 154:1–14.*
Nourel et al., "Quantitiative Determination Of Circulating Soluble Egg Antigen In Urine and Serum of *Schistosoma mansoni*–Infected Individuals Using A Combined Two–Site Enzyme–Linked Immunosorbent Assay," 1994, *Am. J. Trop. Med. Hyg.*, 50(5):585–94.*

(List continued on next page.)

*Primary Examiner*—David S. Romeo
(74) *Attorney, Agent, or Firm*—Fish & Richardson P.C.

(57) ABSTRACT

A method for identifying individuals with a propensity for pathological fibrosis. The method involves providing a sample from an individual with a chronic inflammatory disease, contacting the sample with an antibody specific for fibroblast stimulating factor-1 (FsF-1) under conditions which permit immunocomplex formation, and detecting an increase in the relative level of the immunocomplex as an indication of a propensity for pathological fibrosis. FsF-1 polypeptides and antibodies specific for FsF-1, and DNA sequences encoding FsF-1 polypeptides are also disclosed.

4 Claims, 17 Drawing Sheets-

OTHER PUBLICATIONS

Perlman, et al., "A Putative Signal Peptidase Recognition Site and Sequence in Eukaryotic and Prokaryotic Signal Peptides," 1983, *J. Mol. Biol.*, 167:391–409.*

Prakash et al., Fibroblast Stimulation in Schistosomiasis: IX. Schistosomal Egg Granulomas from Congenitally Athymic Mice are Deficient in Production of Fibrogenic Factors, 1990, *J. Immunology*, 144:317–22.*

Sher et al., "Interleukin 5 is required for the blood and tissue eosinophilia but not granuloma formation induced by infection with *Schistosoma mansoni*," 1990, *Proc. Nat'l Acad. Sci USA*, 87:61–65.*

Tony et al., "Role Of Membrane Immunoglobulin (Ig)–Mediated Major Histocompatibility–Restricted T Cell–B Cell Cooperation," 1985, *J. Exp. Med. @ The Rockefeller University Press*, 162:1695–708.*

Wahl et al., "Modulation of Fibroblast Growth and Function by Monokines and Lymphokines", 1981, *Lymphokines*, 2:179–201.*

Wyler, et al. Mesenchymal Target Cell Specificity of Egg Granuloma–Derived Fibroblast Growth Factor in Schistosomiasis, 1987, *The Journal of Infectious Diseases*, 155(4):728–35.

Wyler, "Hepatic Fibrosis in Schistosomiasis: Egg Granulomas Secrete Fibroblast Stimulating Factor in vitro," 1978, *Science*, 202:438–40.

American Journal of Tropical Medicine and Hygiene, "Differences in Hepatic Firbrosis and Granuloma Size in Several Strains of Mice with Schistosoma Japonicum", 33:602–607, 1984.

Wyler et al., The Journal of Immunology, "Fibroblast Stimulation in Schistosomiasis", 129:1706–1710, 1982.

Wahl et al., The Journal of Immunology, "Lymphocyte–Mediated Activation of Fibroblast Proliferation and Collagen Production", 121:942–946, 1978.

Schmidt et al., The Journal of Immunology, "Interleukin 1, A Potential Regulator of Fibroblast Proliferation", 128:2176–2182, 1982.

Vilcek et al., J. of Exp. Medicine, "Fibroblast Growth Enhancing Activity of Tumor Necrosis Factor and its Relationship to other Polypeptide Growth Factors", 163:632–643, 1986.

The New England Journal of Medicine, "Selective Primary Health Care", 301:967–974, 1979.

Burgess et al., Annu. Rev. Biochem., "The Heparin–Binding (Fibroblast) Growth Factor Family of Proetins", 58:575–606, 1989.

Leof et al., Proceedings of the National Academy of Sciences, "Induction of c–sis mRNA and activity similar to platelet–derived growth factor by transforming growth factor B . . . ", 83:2453–57.

Lobb et al., J. Biol. Chem., "Purification and Characterization of Heparin–binding Endothelial Cell Growth Factors", 261:1924–1928, 1986.

The Journal of Biological Chemistry, "Purification of the Fibroblast Growth Factor Activity from Bovine Brain", 253:3736–3743, 1978.

Gospodarowicz et al., J. of Biol. Chem., "Purification of a Fibroblast Growth Factor from Bovine Pituitary" 250:2515–2520, 1975.

Sugarman et al., Science, "Recombinant Human Tumor Necrosis Factor–α: Effects on Proliferation of Normal and Transformed Cells in Vitro", 230:943–945, 1985.

Higashiyama et al., Science, "A Heparin–Binding Growth Factor Secreted by Macrophage–Like Cells that is related to EGF", 251:936–939, 1991.

Wyler et al., J. of Immun., "Fibroblast Stimulation in Schistosomiasis", 132:3142–3148, 1984.

Wyler et al., J. of Immun., "Fibroblast Stimulation in Schistosomiasis", 130:1371–1375, 1983.

Massague, J. of Biol. Chem., "Subunit Structure of a High–affinity Receptor for Type B–transforming Growth Factor", 260:7059–7066, 1985.

Tropical Disease Bulletin, "Progress in Assessment of Morbidity Due to *Schistosoma Mansoni* Infection", 85:2658–2932, 1988.

Reviews of Infectious Diseases, "Fibronectin in Parasitic Diseases", 9:s391–s399, 1987.

Wyler et al., J. of Infectious Diseases, "Fibroblast Stimulation in Schistosomiasis. I. Stimulation in vitro of Fibroblasts by Soluble Products of Egg Granulomas", 144:254–262, 1981.

Wyler et al., Infection and Immunity, "Direct and indirect Effects of Soluble Extracts of *Schistosoma mansoni* Eggs on Fibroblast Proliferation in vitro", 38:103–108, 1982.

Catty et al., "Production and Quality Control of Polyclonal Antibodies", A Practical Approach, Antibodies, vol. 1, IRL Press, pp. 18–79, 1989.

Prakash et al., J. of Immunol., "Fibroblast Stimulation in Schistosomiasis: XII. Identification of CD4+ Lymphocytes within Schistosomal Egg . . . ", 148:3583–3587, 1992.

Prakash et al., J. of Immunol., "Fibroblast Stimulation in Schistosomiasis: XI. Purification to Apparant Homogeneity of Fibroblast–Stimulating Factor–1, . . . " 146:1679–1684, 1991.

W.E. Paul, Fundamental Immunology, published by Raven Press, Ltd., pp. 455–458, 1993.

Wyler et al., J. of Immunol., "Fibroblast Stimulation in Schistosomiasis: II. Functional and Biochemical Characteristics of Egg Granuloma–Derived Fibroblast–Stimulating Factor", 129:1706–1710, 1982.

Wyler et al., J. of Immunol., "Fibroblast Stimulation in Schistosomiasis: V. Egg Granuloma Macrophages Spontaneously Secrete a Fibroblast–Stimulating Factor", 132:3142–3148, 1984.

Prakash et al., Proc. of the Nat'l. Acad. of Science, USA, "Cloning and Analysis of Murine cDNA that Encodes a Fibrogenic Lymphokine, Fibrosin", 92:2154–2158, 1995.

T.L. Bonfield, J. of Biom. Mat. Res., "Protein Adsorption of Biomedical Polymers Influences Activated Monocytes to Produce Fibroblast Stimulating Factors", 26:457–465, 1992.

Suggs et al., Proc. of the Nat'l. Acad. of Science, USA, "Use of Synthetic Oligonucleotides as Hybridization Probes: . . .", 78:6613–6617, 1981.

Young et al., Proc. of the Nat'l. Acad. of Science USA, "Efficient Isolation of Genes by Using Antibody Probes", 80:1194–1198, 1983.

Lodish et al., Molecular Cell Biology, published by te W.H. Freeman and Company Publishing Co., pp. 222–234, 1995.

D.J. Wyler, Parasitology Today, "Why Does Liver Fibrosis occur in Schistosomiasis?", 8:277–279, 1992.

D.J. Wyler, The New Biologist, "Schistosomes, Fibroblasts, and Growth Factors: How a Worm Causes Liver Scarring", 3:734–740, 1991.

Wyler et al., J. of Infect. Diseases, "Mesenchymal Target Cell Specificity of Egg Granuloma–Derived Fibroblast Growth Factor in Schistosomiasis", 155:728–736, 1987.

D.J. Wyler, Science, "Hepatic Fibrosis in Schistosomiasis: Egg Granulomas Secrete Fibroblast Stimulating Factor in Vitro", 202:438–440, 1978.

Din et al., Amer. J. of Trop. Med. Hyg., "Quantitative Determination of Circulating Soluble Egg Antigen in the Urine and Serum of Schistosoma . . . ", 50:585–594, 1994.

Prakash et al., J. of Immunol., "Fibroblast Stimulation in Schistosomiasis: IX. Schistosomal Egg Granulomas from Congenitally Athymic Mice . . . ", 144:317–322, 1990.

Sher et al., Proc. of the Nat'l. Acad. of Sci. USA, "Interleukin 5 is Required for the Blood and Tissue Eosinophilia . . . ", 87:61–65, 1990.

* cited by examiner

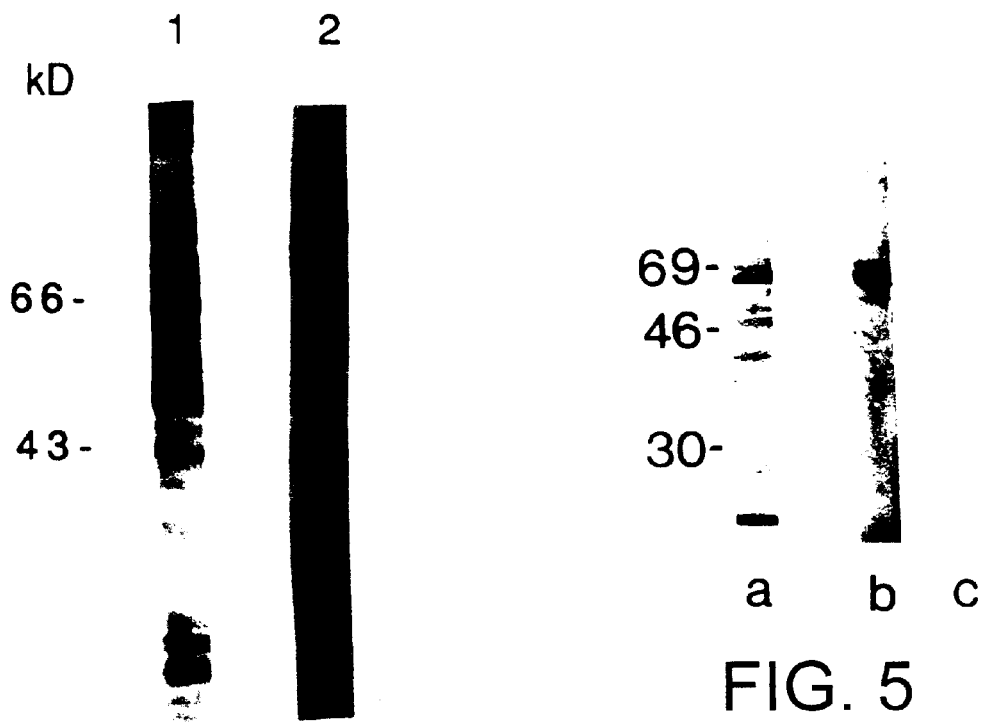
FIG. 4
FIG. 5
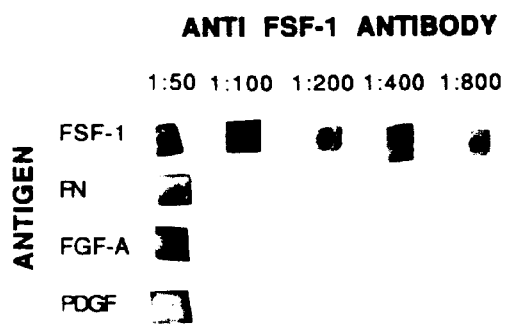
FIG. 6A
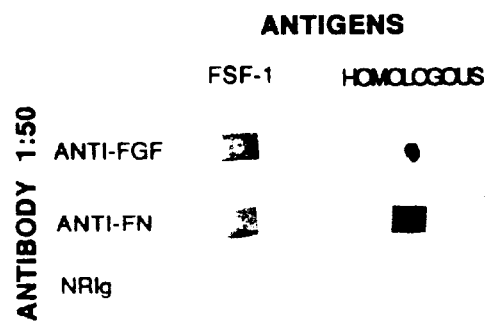
FIG. 6B

```
ATG TTG CCT TTA CTT CTA GGC CTG TAC GGA AGT GTT ACT TCT GCT
Met Leu Pro Leu Leu Leu Gly Leu Tyr Gly Ser Val Thr Ser Ala   15

CTA AAA GCT GCT GCA CCC CCC CCC CCA*AGG GCC TCT AGG CCC
Leu Lys Ala Ala Ala Pro Pro Pro Pro Arg Ala Ser Arg Pro       30

TTG GCC TGC CTC CCC AAG GGC TCA CTA AGC CAG AGG CCA AAG TGC
Leu Ala Cys Leu Pro Lys Gly Ser Leu Ser Gln Arg Pro Lys Cys   45

CCC CCT CCC TTT CGC CTA CCA CCC AAG TTC TCA TGC CCT CCG AGG
Pro Pro Pro Phe Arg Leu Pro Pro Lys Phe Ser Cys Pro Pro Arg   60

GCT GAG GAA GGA GGA ACT AAA GGA ATA GGG GTT TCA TGT ACA TAT
Ala Glu Glu Gly Gly Thr Lys Gly Ile Gly Val Ser Cys Thr Tyr   75

TTA TCA CCC CTT CCA CAA ATC CCC CAG ACC TTT TGT ACA TTT TTA
Leu Ser Pro Leu Pro Gln Ile Pro Gln Thr Phe Cys Thr Phe Leu   90

CAG GGG TGC CCC TCC CTA TAA
Gln Gly Cys Pro Ser Leu STOP
```

FIG. 18

MOUSE FIBROSIN cDNA

```
                    TTCCCCATACCTTGTGACAAAAGTCCTAGGGCTGAAGTTTTT
AAGCCAGGGTTGGAAGGCAAAGGTCACAATTTC-ATG-GTC-ATC-TCT-GAA-GTC-
-TG
 -GAC-CTG-GGA-ATA-GAA-TCC-CCA-GAC-CCC-CCC-CCC-CCC-CCA-CAC-ACA
 -CAC-ACA-TAC-ACA-CAC-ACA-CAC-ACA-CAC-ACA-CAC-ACG-CAA-GTA-TCT
 -CGT-GGA-CTG-TGG-GGT-CAC-TGG-GAG-GAC-AGA-GGT-CAC-TAG-CCT-CTA
 -GAG-AGA-AGT-GTG-TGC-GTG-TGC-ATG-AGG-GGG-TTA-TTT-CAG-AGG-TTA
 -TGG-CTC-ATG-ACT-TAA-GGT-GCA-CCA-ATG-CCC-CCT-CTA-AGG-GCC-
TCT
 -AGG-CCC-TTG-GCC-TGC-CTC-CCC-AAG-GGC-TCA-CTA-AGC-CAG-AGG-CCA
 -AAG-TGC-CCC-CCT-CCC-TTT-CGC-CTA-CCA-CCC-AAG-TTC-TCA-TGC-CCT
 -CCG-AGG-GCT-GAG-GAA-GGA-GGA-ACT-AAA-GGA-ATA-GGG-GTT-TCA-TGT
 -ACA-TAT-TTA-TCA-CCC-CTT-CCA-CAA-ATC-CCC-CAG-ACC-TTT-TGT-ACA
 -TTT-TTA-CAG-GGG-TGC-CCC-TCC-CTA-TAA-
    TTCCCTTCCTGGTTAATTAAATCCTCAGACTGGAAAAAAAAAA
```

FIG. 25

HUMAN FIBROSIN cDNA          AAGCCAGGGTTGGAAGGCAAAGGTCACA

ACCTCACCAGCCACCTCTGAGGTC-ATG-GAA-CCT-GGG-AAC-AGA-AGC-CTC-AAC

-CCC-CAC-AAG-ACC-AAG-CAT-CAC-ATG-GAG-TGT-AGG-GTC-ACT-GGG-AGA

-GCA-GAG-GTC-ACA-GCC-TCT-AGA-GAA-GGG-AGA-GGG-GCG-TGT-GCA-TGG

-GAG-TGT-GGC-TCA-TCT-CGG-GGG-CCA-TGG-GGC-CTC-CTG-AGG-TAC-ACC

-TTT-GCC-CCT-GTA-AGG-GCC-TCT-AGG-CCC-TGG-GCC-TGC-CTC-CCC-AAG

-GGC-TCA-CTA-AGC-CAG-AGG-CCA-AAG-TGC-CCC-CTC-CCG-TTC-ACC-TAC

-CAC-CCA-AGT-CCT-CAT-GCC-CTC-CGA-GGG-CTG-GGG-GAG-GAG-GGG-CTC

-AAG-GAA-GGG-GGG-TTC-CAT-GTA-CAT-ATT-TAT-CAC-CCC-TTT-CAC-ATA

-GCC-CCA-AGA-CCT-TTT-GTA-CAT-TTT-TAC-AGG-GGT-GCC-CCT-CCC-AAC

-AGT-TCC-CTT-CCT-GGT-TAA-TTAAATCCTCAGACTGGAAAAAAAAAA

FIG. 26

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
        (A) LENGTH: 291 base pairs
        (B) TYPE: nucleic acid
        (C) STRANDEDNESS: single
        (D) TOPOLOGY: linear (ii) MOLECULE TYPE: DNA (ix) FEATURE:

(A) NAME/KEY: Coding Sequence
        (B) LOCATION: 1...288

(xi) SEQUENCE DESCRIPTION: SEQ ID NO:1:

```
ATG TTG CCT TTA CTT CTA GGC CTG TAC GGA AGT GTT ACT TCT GCT CTA        48
Met Leu Pro Leu Leu Leu Gly Leu Tyr Gly Ser Val Thr Ser Ala Leu
  1               5                  10                  15

AAA GCT GCT GCA CCC CCC CCC CCC CCA AGG GCC TCT AGG CCC TTG GCC        96
Lys Ala Ala Ala Pro Pro Pro Pro Pro Arg Ala Ser Arg Pro Leu Ala
                 20                  25                  30

TGC CTC CCC AAG GGC TCA CTA AGC CAG AGG CCA AAG TGC CCC CCT CCC       144
Cys Leu Pro Lys Gly Ser Leu Ser Gln Arg Pro Lys Cys Pro Pro Pro
             35                  40                  45

TTT CGC CTA CCA CCC AAG TTC TCA TGC CCT CCG AGG GCT GAG GAA GGA       192
Phe Arg Leu Pro Pro Lys Phe Ser Cys Pro Pro Arg Ala Glu Glu Gly
         50                  55                  60

GGA ACT AAA GGA ATA GGG GTT TCA TGT ACA TAT TTA TCA CCC CTT CCA       240
Gly Thr Lys Gly Ile Gly Val Ser Cys Thr Tyr Leu Ser Pro Leu Pro
 65                  70                  75                  80

CAA ATC CCC CAG ACC TTT TGT ACA TTT TTA CAG GGG TGC CCC TCC CTA       288
Gln Ile Pro Gln Thr Phe Cys Thr Phe Leu Gln Gly Cys Pro Ser Leu
                 85                  90                  95

TAA                                                                    291
```

(2) INFORMATION FOR SEQ ID NO:2:

(i) SEQUENCE CHARACTERISTICS:
        (A) LENGTH: 571 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

```
TTCCCCATAC CTTGTGACAA AAGTCCTAGG GCTGAAGTTT TTAAGCCAGG GTTGGAAGGC        60
AAAGGTCACA ATTTCATGGT CATCTCTGAA GTCATGGACC TGGGAATAGA ATCCCCAGAC       120
CCCCCCCCCC CCCCACACAC ACACACATAC ACACACACAC ACACACACAC ACACACGCAA       180
GTATCTCGTG GACTGTGGGG TCACTGGGAG GACAGAGGTC ACTAGCCTCT AGAGAGAAGT       240
GTGTGCGTGT GCATGAGGGG GTTATTTCAG AGGTTATGGC TCATGACTTA AGGTGCACCA       300
ATGCCCCCTC TAAGGGCCTC TAGGCCCTTG GCCTGCCTCC CCAAGGGCTC ACTAAGCCAG       360
AGGCCAAAGT GCCCCCCTCC CTTTCGCCTA CCACCCAAGT TCTCATGCCC TCCGAGGGCT       420
GAGGAAGGAG GAACTAAAGG AATAGGGGTT TCATGTACAT ATTTATCACC CCTTCCACAA       480
ATCCCCCAGA CCTTTTGTAC ATTTTTACAG GGGTGCCCCT CCCTATAATT CCCTTCCTGG       540
TTAATTAAAT CCTCAGACTG GAAAAAAAAA A                                     571
```

(2) INFORMATION FOR SEQ ID NO:3:

(i) SEQUENCE CHARACTERISTICS:
        (A) LENGTH: 483 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

```
AAGCCAGGGT TGGAAGGCAA AGGTCACAAC CTCACCAGCC ACCTCTGAGG TCATGGAACC        60
```

```
TGGGAACAGA AGCCTCAACC CCCACAAGAC CAAGCATCAC ATGGAGTGTA GGGTCACTGG      120

GAGAGCAGAG GTCACAGCCT CTAGAGAAGG GAGAGGGGCG TGTGCATGGG AGTGTGGCTC      180

ATCTCGGGGG CCATGGGGCC TCCTGAGGTA CACCTTTGCC CCTGTAAGGG CCTCTAGGCC      240

CTGGGCCTGC CTCCCCAAGG GCTCACTAAG CCAGAGGCCA AAGTGCCCCC TCCCGTTCAC      300

CTACCACCAA GTCCTCATGC CCTCCGAGGG CTGGGGAGG AGGGGCTCAA GGAAGGGGG       360

TTCCATGTAC ATATTTATCA CCCCTTTCAC ATAGCCCCAA GACCTTTTGT ACATTTTTAC      420

AGGGGTGCCC CTCCCAACAG TTCCCTTCCT GGTTAATTAA ATCCTCAGAC TGGAAAAAAA      480

AAA                                                                   483
```

(2) INFORMATION FOR SEQ ID NO:4:

(i) SEQUENCE CHARACTERISTICS:
        (A) LENGTH: 194 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

```
CTCACTAAGC CAGAGGCCAA AGTGCCCCCC TCCCTTTCGC CTACCACCCA AGTTCTCATG       60

CCCTCCGAGG GCTGAGGAAG GAGGAACTAA AGGAATAGGG GTTTCATGTA CATATTTATC      120

ACCCCTTCCA CAAATCCCCC AGACCTTTTG TACATTTTTA CAGGGGTGCC CCTCCCTATA      180

ATTCCCTTCC TGGT                                                       194
```

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

```
CTCACTAAGC CAGAGGCCAA AGTG                                             24
```

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

```
ACCAGGAAGG GAATTATAGG GAGG                                             24
```

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

CCTTTAGTTC CTCCTTCCTC AGCC                                              24

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

CATGAGAACT TGGGTGGTAG GCGA                                              24

(2) INFORMATION FOR SEQ ID NO:9:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

AAGCCAGGGT TGGAAGGCAA AGGTCACA                                          28

(2) INFORMATION FOR SEQ ID NO:10:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

TTTTTTTTTT CCAGTCTGAG GATTTAATTA ACCAG                                  35

(2) INFORMATION FOR SEQ ID NO:11:

(i) SEQUENCE CHARACTERISTICS:
        (A) LENGTH: 96 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:11:

Met Leu Pro Leu Leu Leu Gly Leu Tyr Gly Ser Val Thr Ser Ala Leu
 1               5                   10                  15

Lys Ala Ala Ala Pro Pro Pro Pro Arg Ala Ser Arg Pro Leu Ala
                20                  25                  30

Cys Leu Pro Lys Gly Ser Leu Ser Gln Arg Pro Lys Cys Pro Pro Pro
            35                  40                  45

Phe Arg Leu Pro Pro Lys Phe Ser Cys Pro Pro Arg Ala Glu Glu Gly
        50                  55                  60

-continued

```
Gly Thr Lys Gly Ile Gly Val Ser Cys Thr Tyr Leu Ser Pro Leu Pro
 65                  70                  75                  80

Gln Ile Pro Gln Thr Phe Cys Thr Phe Leu Gln Gly Cys Pro Ser Leu
                 85                  90                  95
```

FIBROBLAST STIMULATING GROWTH FACTOR 1 (FSF-1) AND THE EARLY DETECTION OF FIBROSIS

This is a divisional of application Ser. No. 08/395,674, abandoned, filed on Feb. 28, 1995, which is a continuation-in-part of application Ser. No. 08/152,904, abandoned, filed on Nov. 15, 1993, which is a continuation of application Ser. No. 07/840,426, abandoned, filed on Feb. 24, 1992.

This invention was supported by United Public Health Service grant R22 AI 17615. The government has certain rights in the invention.

BACKGROUND OF THE INVENTION

The field of the invention is lymphokines and fibrosis.

Schistosomiasis is one of the most important helminthic diseases, estimated to afflict 200 million people in the tropics (Walsh et al., 1979). Two of the schistosome species that infect humans (*Schistosoma mansoni* and *S. japonicum*) can cause serious morbidity (including portal hypertension and gastrointestinal hemorrhage) as a result of a form of hepatic fibrosis (Cheever et al., 1967). However, only a relatively small subpopulation (3–6%) of infected individuals develop this scarring; the others remain generally healthy (Chen et al., 1988).

Traditional forms of antihelminthic therapy have a number of undesirable side effects, and treatment with the relatively new drug, praziquantel, is very expensive, thus making antihelminthic treatment of all infected individuals impractical. In addition, while early antihelminthic therapy may aid in preventing liver scarring, it has not been established that this is an invariable outcome of treatment (Homeida et al., 1988).

Alternatively, early aggressive treatment of infected individuals with anti-inflammatory or immunosuppressive drugs including methotrexate, cytotoxins and various corticosteriods may aid the prevention of scarring. However, given that these drugs are known to produce a number of relatively severe side effects, treatment of all infected individuals, 94–97% of which would never develop the progressive fibrotic form of the disease, is both undesirable and impractical.

Several other chronic inflammatory diseases, including pulmonary fibrosis, scleroderma/progressive systemic sclerosis, sarcoidosis, sclerosing cholangitis, primary biliary cirrhosis and inflammatory bowel disease also can result in organ dysfunction due to pathological fibrosis. As in schistosomiasis, only a subpopulation of individuals with these diseases develop debilitating organ scarring. Thus, methods are needed that would make it possible to predict which patients will develop the progressive fibrotic forms of these inflammatory diseases so that more aggressive, anti-fibrotic courses of treatment can be limited to only those individuals who would benefit from these treatments.

SUMMARY OF THE INVENTION

In general, the invention features a method for identifying individuals with a propensity for pathological fibrosis. The method comprises providing a sample from an individual with a chronic inflammatory disease, contacting the sample with an antibody specific for FsF-1 under conditions which permit immunocomplex formation, and detecting an increase in the relative level of the immunocomplex as an indication of a propensity for pathological fibrosis. By "relative level" is meant the relative amount of immunocomplex detected when compared to the level in a sample from a normal individual.

In an individual at a chronic stage of the disease, an increased level of the immunocomplex in a single sample is indicative that they are at risk of serious fibrosis. In an individual at an early stage of the disease, the method further involves providing serial samples from the individual over a period of time (e.g., every 3 to 6 months over a period of 1 to 3 years), and detecting a persistent increase in the relative level of the immunocomplex as an indication of a propensity for pathological fibrosis.

The sample may be any biological sample. Preferably, the sample is a blood, serum or plasma sample, but may also be a urine sample; a tissue sample (e.g., biopsy); an effusion obtained from a joint, the abdominal cavity (e.g., ascites), pleural fluid, cerebral spinal fluid, and the aqueous humor; or from the supernatant of cultured peripheral blood mononuclear cells. Also preferably, the sample is obtained from a mammal, and even more preferably, the mammal is a human.

In one preferred embodiment, the pathological scarring results from hepatic fibrosis. In another related embodiment, hepatic fibrosis is the result of the disease schistosomiasis. In other embodiments, the pathological fibrosis is a result of various chronic inflammatory diseases including sarcoidosis, scleroderma, sclerosing cholangitis, rheumatoid arthritis, pulmonary fibrosis, and interstitial pneumonitis.

The invention also features a substantially pure fibroblast stimulating factor-1 (FsF-1) polypeptide. By "FsF-1 polypeptide" is meant all or part of a novel lymphokine, also referred to as fibrosin, that is a heparin-binding growth factor which stimulates fibroblast proliferation, collagen and hyaluronan synthesis and fibroblast chemotaxis, and which is distinct from other previously characterized heparin-binding growth factors. Preferably, FsF-1 is produced in $CD4^+$ lymphocytes, and the naturally occurring intact polypeptide is characterized as being of molecular weight of about 60 kD as measured by SDS-PAGE, and being of isoelectric point of about 6.2. By "polypeptide" is meant any chain of amino acids, regardless of length or post-translational modification (e.g., glycosylation).

A further feature of the invention is a substantially pure antibody which specifically binds FsF-1. By "specifically binds" is meant an antibody which binds to FsF-1 and which does not substantially recognize and bind to other antigenically-unrelated molecules. Antibodies according to the invention may be prepared by a variety of methods. For example, the FsF-1 protein or antigenic fragments thereof can be administered to an animal in order to induce the production of polyclonal antibodies. Alternatively, antibodies according to the invention may be monoclonal antibodies. Such monoclonal antibodies can be prepared using hybridoma technology (see, e.g., Kohler et al., *Nature* 256:495, 1975; Kohler et al., *Eur. J. Immunol.* 6:511, 1976; Kohler et al., *Eur J. Immunol.* 6:292, 1976; Hammerling et al., *In Monoclonal Antibodies and T Cell Hybridomas*, Elsevier, N.Y., 1981).

As used herein, the term "substantially pure" describes a compound, e.g., a protein, polypeptide, or antibody, that is substantially free from the components that naturally accompany it. Typically, a compound is substantially pure when at least 60%, more preferably at least 75%, more preferably at least 90%, and most preferably at least 99%, of the total material (by weight) in a sample is the compound of interest. Purity can be measured by any appropriate method, e.g., in the case of polypeptides by column chromatography, polyacrylamide gel electrophoresis, or HPLC analysis.

The FsF-1 polypeptide, according to the invention, may be used as the active ingredient of therapeutic compositions.

In such therapeutic compositions, the active ingredient may be formulated with a physiologically-acceptable carrier or anchored in the membrane of a cell. Such therapeutic compositions are used to stimulate fibroblast proliferation and extracellular matrix synthesis, e.g., to promote wound healing. The method involves applying the therapeutic composition, preferably topically, to a wound of a mammal in a dosage effective to stimulate fibroblast proliferation and thereby accelerate wound closure.

In another aspect, the invention also features isolated DNA consisting essentially of a DNA sequence encoding an FsF-1 polypeptide of a vertebrate animal, preferably a mammal, which polypeptide has an amino acid sequence with at least 50% (preferably 60%, more preferably at least 70%, and most preferably at least 85%) homology to the amino acid sequence encoded by the nucleotide sequence shown in FIG. 18 (SEQ ID NO.: 1), FIG. 25 (SEQ ID NO.: 2) or FIG. 26 (SEQ ID NO.: 3).

By "isolated", as used herein in reference to DNA, is meant a DNA that is not immediately contiguous with (i.e., covalently linked to) both of the coding sequences with which it is immediately contiguous in the naturally occurring genome of the organism from which the DNA of the invention is derived. The term therefore includes, for example, a recombinant DNA which is incorporated into a vector (e.g., an autonomously replicating virus or plasmid), or into the genomic DNA of a prokaryote or eukaryote; DNA which exists as a separate molecule independent of other DNA sequences such as a cDNA or genomic DNA fragment produces by chemical means (e.g., polymerase chain reaction, ligase chain reaction), or by restriction endonuclease treatment; and recombinant DNA which is part of a hybrid gene encoding additional polypeptide sequence(s). Also included in the isolated DNAs of the invention are single-stranded DNAs which are generally at least 10 nucleotides long, preferably at least 18 nucleotides long, more preferably at least 30 nucleotides long, and ranging up to full length of the gene or CDNA encoding a FsF-1 polypeptide. The single-stranded DNAs can also be detectably labelled for use as hybridization probes, and can be antisense. Preferably, the isolated DNA hybridizes under conditions of high stringency to all or part of the DNA sequence shown in FIG. 18 (SEQ ID NO.: 1), FIG. 25 (SEQ ID NO.; 2) or FIG. 26 (SEQ ID NO.: 3). By "high stringency" is meant, for example, conditions such as those described herein below for the isolation of human FsF-1 cDNA (also see *Current Protocols in Molecular Biology,* John Wiley & Sons, New York, 1989). Most preferably the animal is a mouse or a human, and the DNA sequence encodes substantially all of the amino acid sequence shown in FIG. 18 (SEQ ID NO.: 1), FIG. 25 (SEQ ID NO.: 2) or FIG. 26 (SEQ ID NO.: 3). The DNA of the invention can be incorporated into a vector [which may be provided as a purified preparation (e.g., a vector separated from the mixture of vectors which make up a library)] containing a DNA sequence encoding an FsF-1 polypeptide of the invention or a fragment of the FsF-1 polypeptide, and a cell or essentially homogenous population of cells (e.g. prokaryotic cells, or eukaryotic cells such as mammalian cells) which contain the vector or the isolated DNA described above. By "essentially homogenous" is meant that at least 99% of the cells contain the vector of the invention (or the isolated DNA). Preferably, the vector is capable of directing expression of an FsF-1 polypeptide (for example, in a cell transfected or transformed with the vector).

A nucleic acid "consisting essentially of" a particular sequence of nucleotides as used herein refers to that particular sequence and other sequences that are identical to the first sequence but for the addition to or removal from the sequence of a few nucleotides (e.g., 2 to 10) which does not alter the amino acid sequence encoded by the nucleic acid. "Homologous", as used herein in reference to DNA or polypeptide molecules, refers to the subunit sequence similarity between two molecules. When a subunit position in both of the molecules is occupied by the same monomeric subunit (i.e., nucleotide or amino acid, respectively), then the molecules are homologous at that position. The homology between two nucleotide or two amino acid sequences is a direct function of the number of matching or homologous position, e.g., if half the positions in two DNA or two amino acid sequences are homologous, then there is a total sequence homology between the molecules of 50%. By "substantially homologous" is meant largely but not wholly homologous (e.g., greater than 80%).

The isolated DNA of the invention can be used to detect the level of mRNA encoding FsF-1 in a sample. The method involves contacting the sample with all or a portion of a single-stranded nucleic acid of the invention under hybridization conditions which allow the formation of nucleic acid duplexes between the nucleic acid and mRNA in the sample, and then determining the amount of duplexes in the sample as an indication of a propensity for tissue fibrosis. The detection of the duplexes can involve any standard techniques for identifying duplex molecules. Preferably, either the nucleic acid of the invention, or the mRNA from the sample are labeled with a chemical moiety which is capable of being detected, including, without limitation, radioactive isotopes, enzymes, luminescent agents, precipitating agents, and dyes.

Individuals skilled in the art will readily recognize that the compositions of the present invention can be assembled in a kit for the detection of FsF-1 polypeptides or mRNA. Typically, such kits include reagents containing the nucleic acids or antibodies of the present invention with instructions and suitable packaging for their use as part of an assay for FsF-1.

In another aspect, the invention features an FsF-1 polypeptide (or an substantially pure preparation thereof), produced by the expression of a recombinant DNA molecule encoding the FsF-1 polypeptide. Preferably, the polypeptide includes a fragment of a naturally occurring FsF-1 polypeptide, and is capable of stimulating the growth, mitogenesis and chemotaxis of fibroblasts according to the assays described herein. More preferably, the polypeptide also stimulates fibroblast extracellular matrix synthesis. Most preferably, the polypeptide included the amino acid sequence depicted in FIG. 18 (SEQ ID NO.: 1).

Pathological fibrosis in schistosomiasis is preceded by a chronic granulomatous inflammatory reaction to helminth eggs deposited in the liver. In patients, there is a well-established association between the presence of severe liver fibrosis and relatively high levels of T-cell responsiveness to schistosomal antigens during chronic infection. This is a striking finding, because such brisk T cell responsiveness—which typically is present in the early stages of the infection—is markedly reduced in many (or most) chronically-infected patients without severe liver fibrosis. These observations indicate that spontaneous down-regulation of anti-schistosomal, especially anti-schistosomal egg antigen (anti-SEA) T cell responses typically occur in chronic infection in patients, whereas persistently high responsiveness contributes to the development of fibrosis.

We have purified a potent fibroblast mitogen, FsF-1, and have demonstrated that this polypeptide is overproduced by the CD4+ cells contained within these egg granulomas. Thus, we have concluded that FsF-1 plays an important role in the progression of fibrotic pathogenesis in liver, and tissue fibrosis in other chronic inflammatory disease.

In addition, FsF-1 is overproduced in lymphocytes of the organ wherein scarring develops, and in relatively high amounts (i.e., compared to animals which do not develop fibrosis) in serum, plasma, blood, urine and serous effusions. Thus, detection of FsF-1 in the lymphocytes from patients with chronic inflammatory diseases using the method of the present invention provides a relatively simple and rapid means to detect those individuals with a propensity to develop the progressive fibrotic forms of these diseases. This provides the advantage of allowing clinicians to limit treatment to only the subpopulation of infected individuals which require antifibrotic and/or antihelminthic therapy.

Unless defined otherwise, all technical and scientific terms used herein have the same meaning as commonly understood by one of ordinary skill in the art to which this invention pertains. All publications mentioned herein are incorporated by reference. Examples of the preferred methods and materials will now be described. These examples are illustrative only, and not intended to be limiting as those skilled in the art will understand that methods and materials similar or equivalent to those described herein can be used in the practice or testing of the present invention.

DETAILED DESCRIPTION

The drawings will first briefly be described.

FIG. 1 is a gel filtration chromatography (Biogel P-30) of unconcentrated egg granuloma culture supernatant. Samples of each fraction were assayed at a final concentration of 1/20 for their ability to stimulate fibroblast proliferation (uptake of [$^3$H]-thymidine). Each point is a mean of three determinations (SEM$\leq$10% of the mean). Elution positions of relevant m.w. standards are indicated. Shown is a representative experiment of more than six experiments.

FIG. 2 is a heparin-Sepharose affinity chromatography of a pool of biologically-active fractions obtained by gel filtration chromatography (Biogel P30) of crude granuloma culture supernatant. Thirty 1-ml fractions were collected. Each fraction was tested for its ability to stimulate fibroblast proliferation. The mean cpm of triplicate determinations is indicated (SEM$\leq$10%). Shown are the results of a representative experiment of two performed.

FIG. 3 is a FPLC anion exchange chromatography of purified FsF-1. The eluted material from heparin-Sepharose was applied to a Mono Q column and eluted at a rate of 1 ml/min with a gradient of NaCl (0 to 2.2 M NaCl). Arrow marks the elution position of commercial heparin. Each point represent the mean of three determination: SEM$\leq$10%. Shown is a representative experiment of two performed.

FIG. 4 is a SDS-PAGE (10% acrylamide) of FsF-1 (lane 2) prepared from granuloma culture supernatants by our published methods and used for immunizing rabbits to prepare anti FSF-1 IgG described in this report. For comparison, the electropherogram of proteins present in unfractionated granuloma supernatant is shown in lane 1. Note that the migration position of FsF-1 (lane 2) corresponds to that of a major protein (MW 60 kD) present in the starting material (lane 1). 10% acrylamide; silver stain.

FIG. 5 is a Western blot of cell-free supernatants from egg granuloma cultures (granuloma supernatant) probed with anti FsF-1 antibody. Granuloma supernatant was subjected to SDS-PAGE, electrophoretically transferred to Immobilon-P Transfer Membranes (Millipore) and then either stained with Coomassie Blue (lane a); or treated with anti FSF-1 IgG (lane b), or pre-immune IgG (lane c), followed by alkaline phosphatase-conjugated goat anti rabbit IgG (Promega Corp., Madiaon, Wis.) and developed with substrate as described. The migration position of standard molecular weight markers is shown.

FIG. 6 is a dot blot ELISA of FsF-1 (10 ng), plasma fibronectin (FN) (20 ng), acidic fibroblast growth factor (FGF) (100 ng, and platelet derived growth factor (PDGF) (40 ng) applied to nitrocellulose paper in a volume of 1 $\mu$l to 5 $\mu$l and then probed with antibodies.

FIG. 7 depicts a heparin-Sepharose eluate (FsF-1:10 ng/ml) or FGF (5 ng/ml) incubated with either normal rabbit IgG (open bar) or with anti-FsF-1 (closed bar) at a final concentration of 2.5 $\mu$g/ml. Remaining fibroblast-mitogenic activity is represented as percent cpm obtained with untreated mitogens. B, PDGF (10 ng/ml), biologically active peak from P-30 chromatography, or heparin-Sepharose eluate (FsF-1:~10 ng/ml) was treated with either normal rabbit IgG (open bar) or anti-PDGF IgG (closed bar; 50 mg/ml). The supernatants were then tested for fibroblast mitogenic activity. Shown is a representative of three performed.

FIG. 8 shows growth of bovine aortic endothelial cells (open symbols) and human fibroblasts (solid symbols) in response to FGF (A) or to heparin-Sepharose purified FsF-1 (B). Growth response was determined by counting numbers of cells per culture after a 96 h incubation. Baseline counts (medium alone) were: fibroblasts, 6.5$\pm$0.1$\times$10$^4$; endothelial cells, 6.1$\pm$0.1 10$^4$. The first two points in B represent responses to FsF-1 at concentrations of 0.01 and 0.1 vol %. Shown is a representative experiment of two performed. Each point represents a mean of four determinations (SEM$\leq$10%).

FIG. 9 is a curvilinear representation of flow cytometry analysis of dissociated granuloma cells stained with NRS plus FITC-conjugated goat anti rabbit IgG (a) or anti FSF-1 IgG followed by FITC-conjugated goat anti rabbit IgG (b).

FIG. 10 is a contour plot of flow cytometry analysis of monodispersed cells obtained from isolated hepatic egg granulomas. Cells enzymatically dissociated from intact granulomas were stained in the following manner and then analyzed with a FACScan: (a) unstained cells; (B) phycoerythrin-conjugated rat anti mouse CD4 antibody; (C) anti FsF-1 IgG followed by FITC- conjugated goat anti rabbit IgG; (D) anti FsF-1 IgG, followed by FITC-conjugated anti rabbit IgG, followed by phycoerythrin conjugated rat anti CD4.

FIG. 11 is an autoradiograph of metabolically-labeled proteins produced by granuloma CD4+ lymphocytes following SDS-PAGE. CD4+ lymphocytes were purified by FACS from suspensions of enzymatically-dissociated granuloma cells and incubated for 24 h in the presence of $^{35}$S-methionine-$^{35}$S-cysteine. Cell-free supernatants were then either subjected to 10% SDS-PAGE directly (lane 1) or were precleared by incubation with Sepharose-conjugated normal rabbit IgG and then treated with anti FsF-1 IgG using two different antibody concentration (5 $\mu$g/mL, lane 2; 15 $\mu$g/mL, lane 3) prior to electrophoresis. The migration position of standard molecular weight markers is indicated.

Figure 14A:
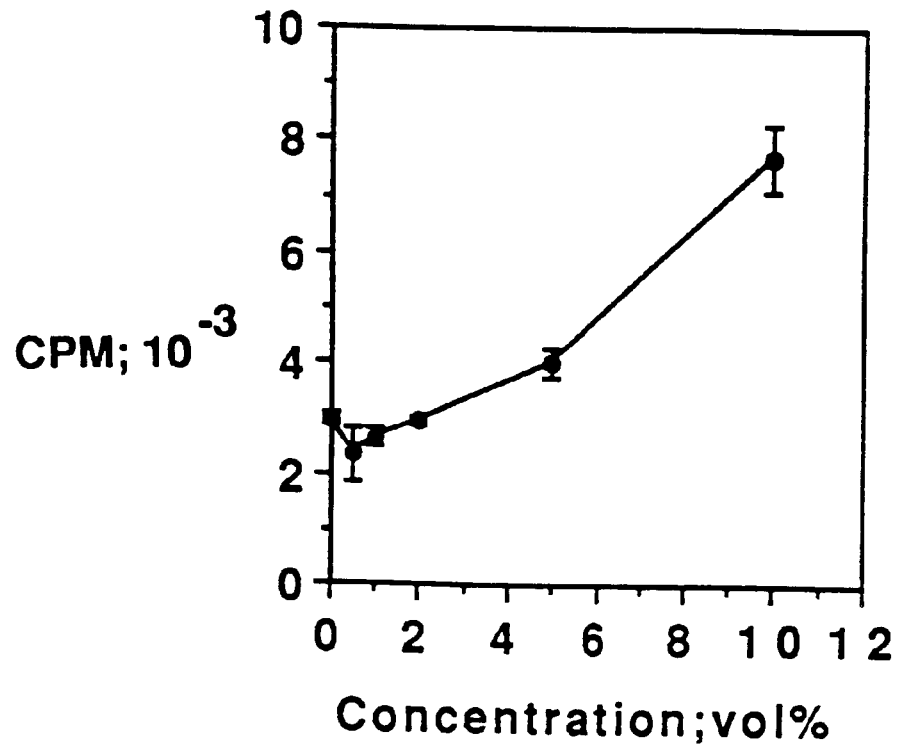
FIG. 14A is a line graph which depicts fibroblast [$^3$H]-thymidine incorporation in response to culture supernatants of CDC25 cells stimulated with concavalin A (con A) for 24 h. Mean±SEM of triplicate determinations is shown for each concentration of culture supernatant tested.
Figure 14B:
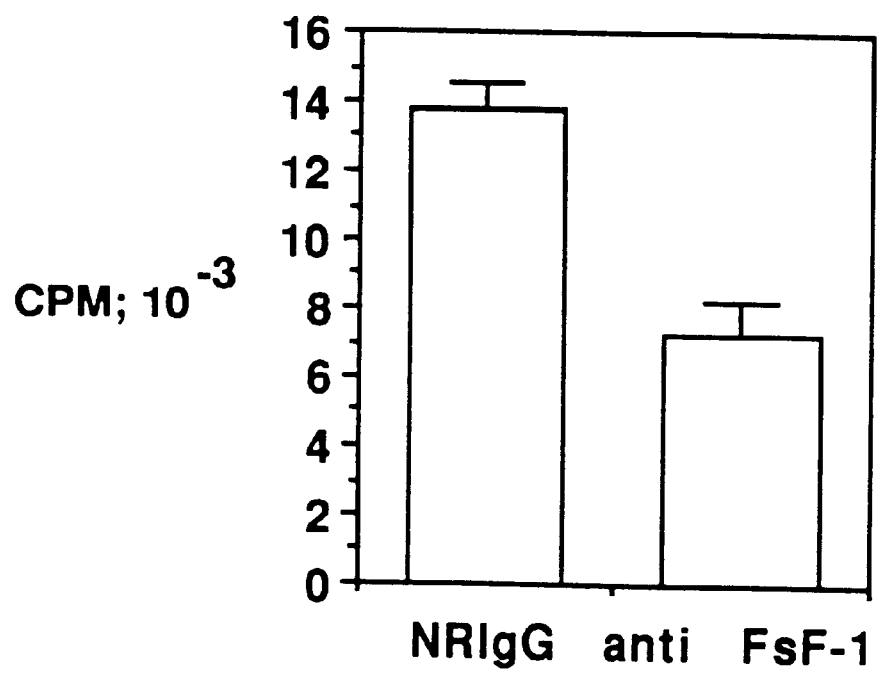

FIG. 14B is a bar graph which demonstrates the partial neutralization of the fibroblast mitogenic activity in CDC25 culture supernatant. Supernatants were incubated for 1 h with either pre-immune, normal rabbit IgG (NRIgG) or rabbit anti FsF-1 IgG at 2.5 µg/ml. The mixture was tested at 5% vol/vol concentration. NRIgG did not affect the response to culture supernatant. Mean±SEM of triplicate determinations is shown.

Figure 15:
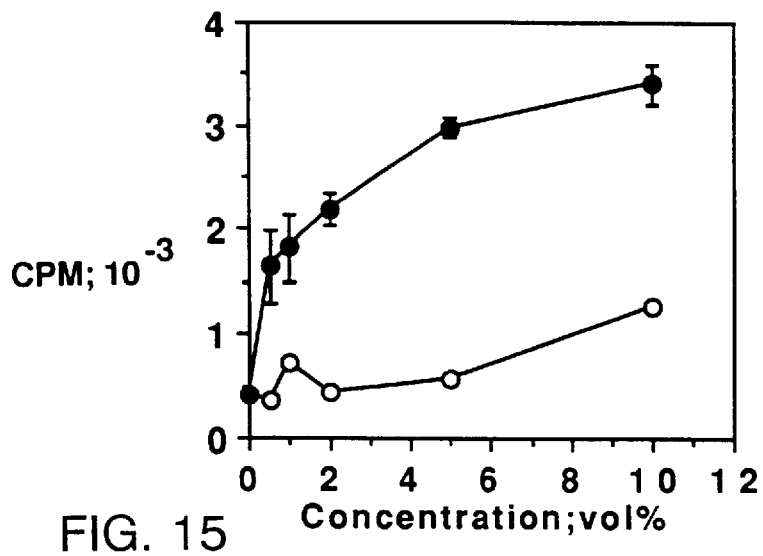

FIG. 15 is a graph which depicts fibroblast [$^3$H]-thymidine incorporation in response to culture supernatants from COS-7 cells transfected with plasmids DNA representing the whole CDC25 cDNA library (closed symbols) and from sham-transfected COS-7 cells (open symbols). Mean±SEM of triplicate determinations is shown for each concentration of culture supernatant shown.

Figure 16A:
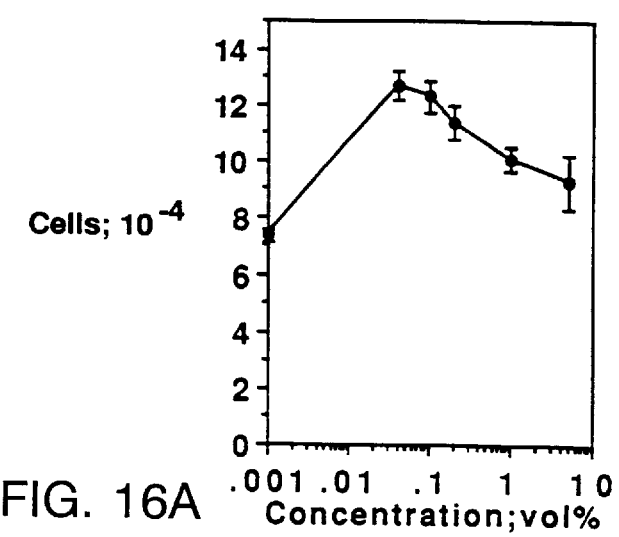

FIG. 16A is a graph which depicts the growth of fibroblasts in response to culture supernatants from COS-7 cells transfected with plasmid DNA containing the clone 2B3 cDNA insert. The mean±SEM of fibroblast cell number determined after 96 h of incubation are shown for each concentration of transfectant culture supernatant tested (indicated on logarithmic scale). Cultures of fibroblasts maintained for 96 h in medium alone contained 6.7±0.3×10$^4$ cells.

Figure 16B:
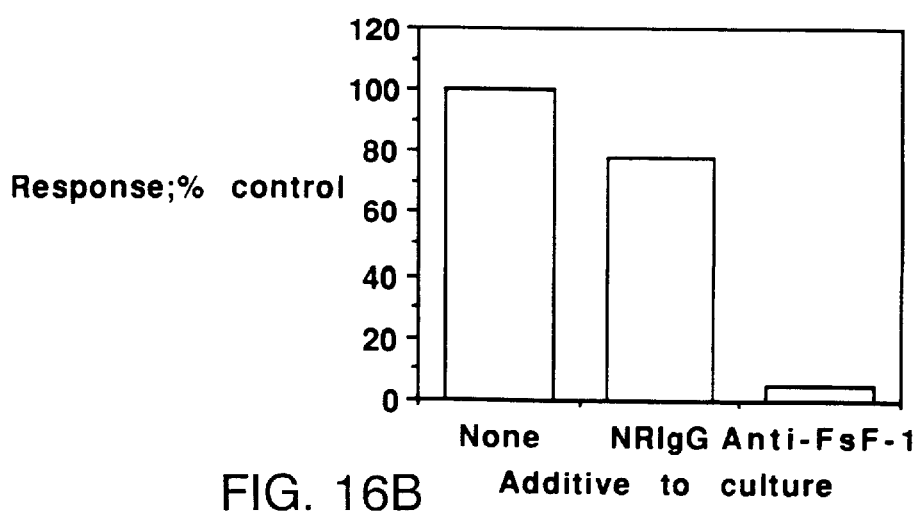

FIG. 16B is a bar graph which depicts the neutralization of fibroblast stimulating activity in culture supernatants of COS-7 cells transfected with clone 2B3-containing plasmid DNA. Supernatants were incubated for 1 h with 7.5 µg/ml of either normal rabbit IgG (NRIgG) or rabbit anti FSF-1 IgG followed by adsorption with protein A-Sepharose and tested at a final concentration of 0.01% vol/vol for the ability to stimulate fibroblast [$^3$H]-thymidine incorporation. The effect of treatments is shown relative to the response of fibroblasts to untreated transfectant culture supernatant tested at 0.01 vol %.

Figure 17:
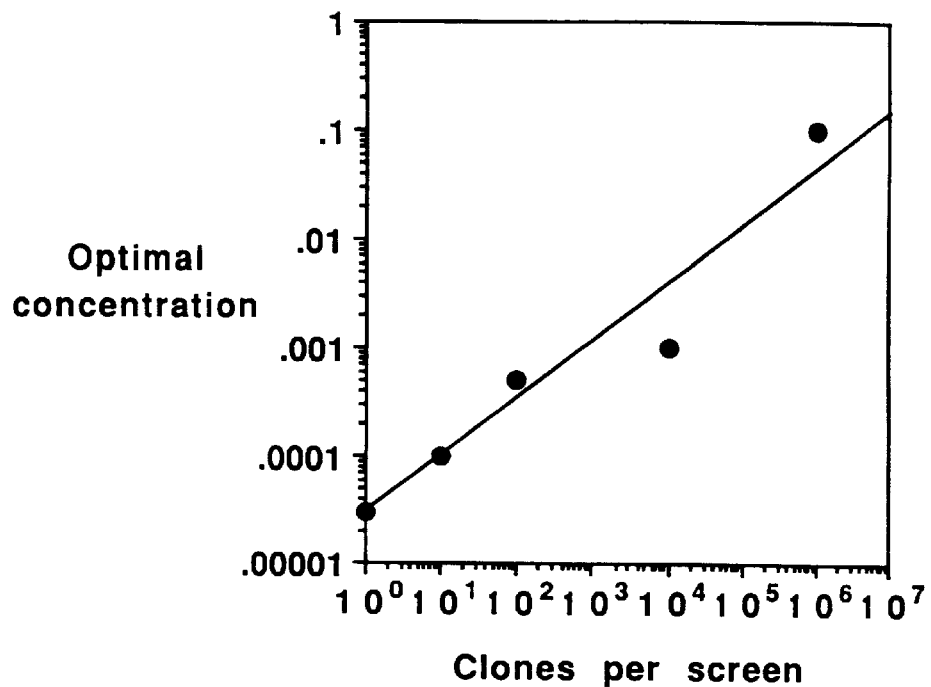

FIG. 17 is a graph which illustrates sib selection in the cloning of 2B3 cDNA that encodes a fibroblast mitogen. COS-7 cells were transfected with plasmid DNA and the transfectant supernatants were tested at various concentrations for their ability to stimulate fibroblast [3H] thymidine incorporation. Following transfection with the entire library cDNA (10$^6$ clones), pools of clones were sequentially screened and selected for their ability to encode biologically active macromolecules. The inverse correlation between the number of clones per screen and the concentration of the corresponding transfectant culture supernatant that maximally stimulated fibroblast responses reflects the progressive enrichment of cDNA that encodes fibrogenic activity.

FIG. 18 illustrates the nucleotide sequence and predicted amino acid sequence of the 2B3 CDNA insert (SEQ ID NO.: 11). Codons 1–25 are derived from the vector; the insert begins with codon AGG (asterisk) and ends with the termination codon TAA (codon 97).

Figure 19:
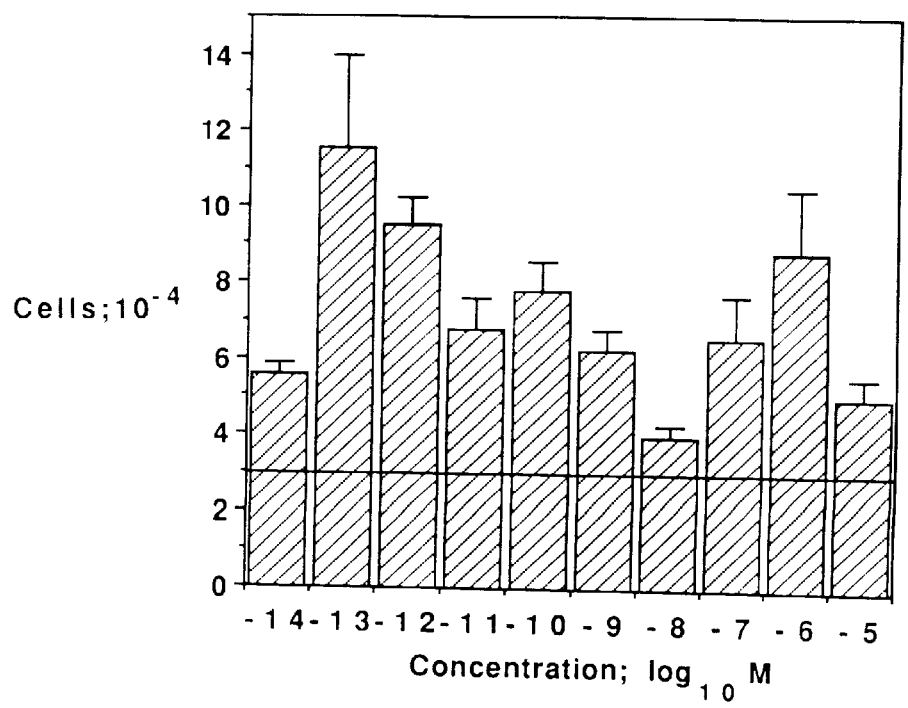

FIG. 19 is a bar graph which depicts fibroblast growth in response to 72 h incubation with various doses of the synthetic 2B3 peptide in the absence of serum. The mean (±SEM) responses of triplicate determinations in a representative experiment are shown. The horizontal line depicts the mean fibroblast number grown in medium alone (baseline). In all, twelve experiments were performed; cells were enumerated at 72 h in 6 and at 96 h in 6. Maximum responses at pM concentrations were 3–4 fold baseline, and 2–3 fold baseline at µM concentrations.

Figure 20:
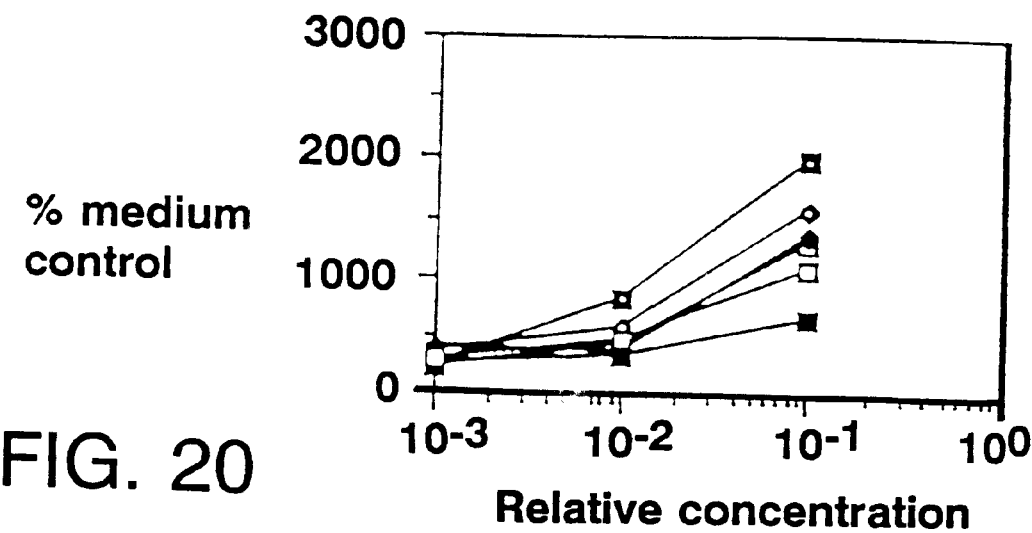

FIG. 20 is a graph depicting the fibroblast mitogenic activity of supernatants from cloned T cell hybridomas stimulated with 10 µg/ml ConA.

Figure 21:
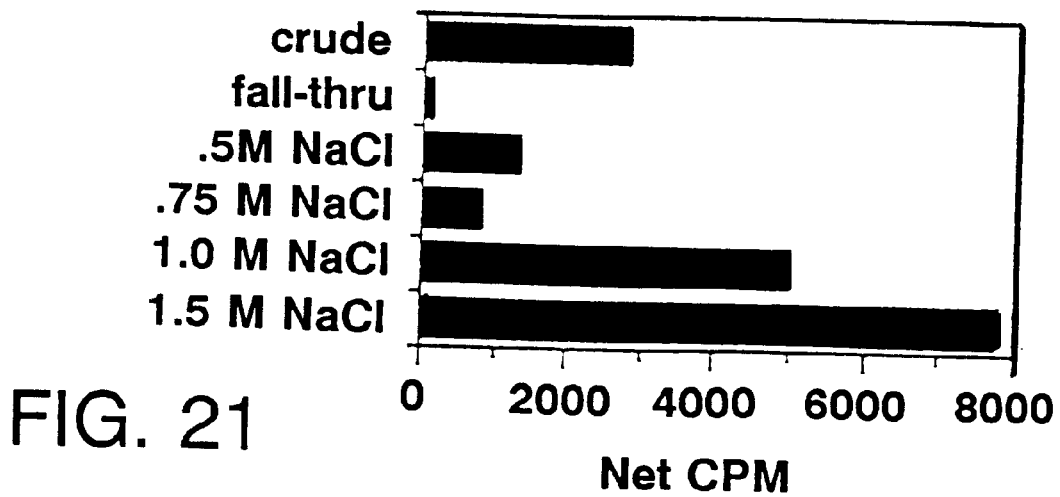

FIG. 21 is a bar graph of the elution profile of the hybridoma-derived mitogen from T hybridoma B12.

Figure 22:
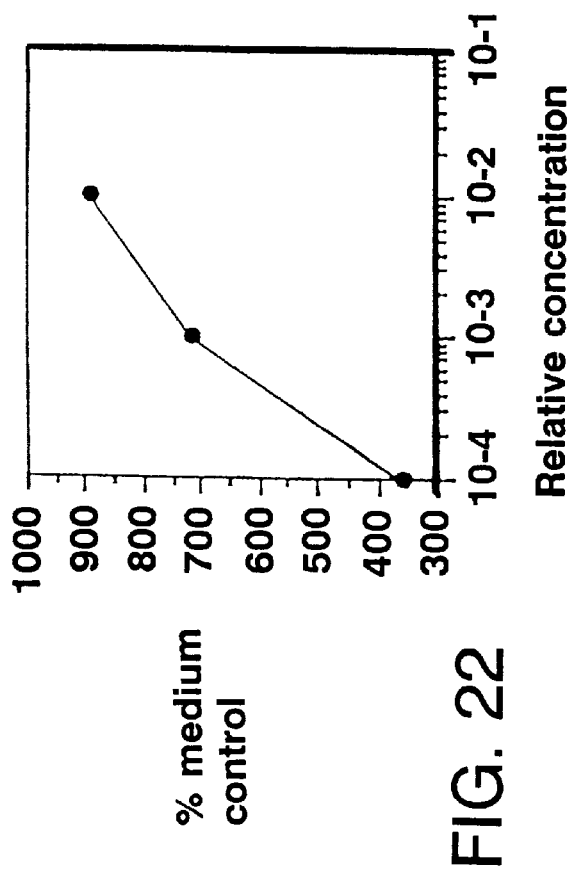

FIG. 22 is a graph depicting the SEA stimulation of FsF-1 production in hybridoma B12.

Figure 23:
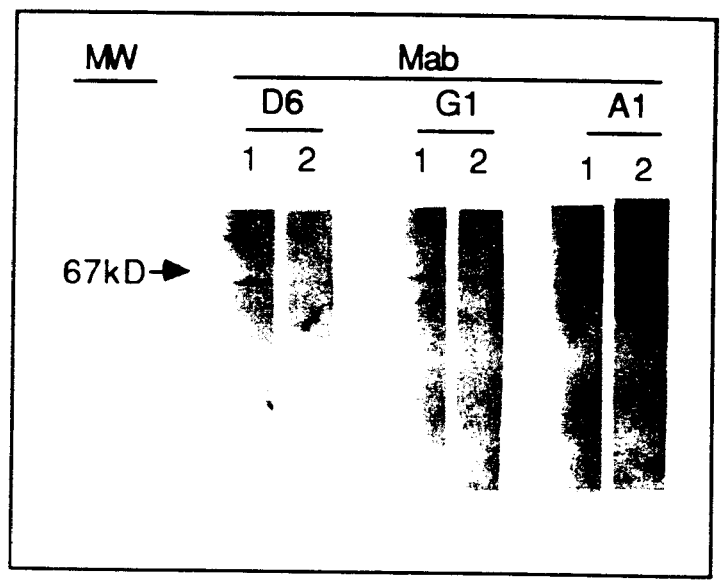

FIG. 23 is a Western Blot of crude supernatants from con A stimulated T cell hybridomas using anti-FsF1 Mabs.

Figure 24:
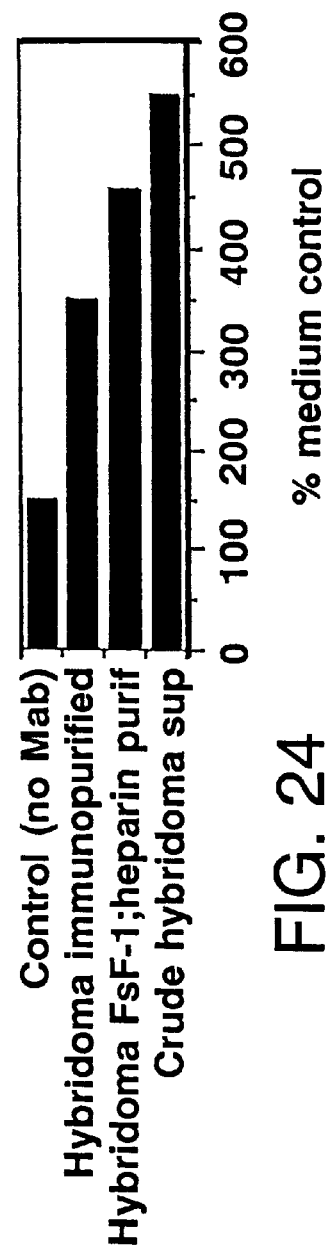

FIG. 24 is a bar graph depicting the immunopurification of mitogenic acitivity with anti-FsF-1 Mab from T hybridoma B12.

FIG. 25 depicts the nucleotide sequence of full-length mouse fibrosin cDNA (SEQ ID NO.: 2). Underlined are the two PCR primers (T2 and B4).

FIG. 26 depicts the nucleotide sequence of the full-length human fibrosin cDNA (SEQ ID NO.: 3).

PURIFICATION AND CHARACTERIZATION OF FSF-1

Animals and schistosomiasis infection C57BL/6NcrLBr female mice (18 to 20 g; Taconic Farms, Inc., Germantown, N.Y.) were infected by the intraperitoneal injection of 35–50 cercariae of S. mansoni (Puerto Rican strain) suspended in 0.5 ml sterile saline. The mice were euthanized eight weeks later by inducing $CO_2$ narcosis and their livers were placed in cold Hanks' buffered salt solution (HBSS).

Isolation of granulomas and preparation of granuloma supernatant.

Isolation of granulomas was performed as described previously (Wyler et al., Science, 202:438 (1978), Pellegrino et al., J. Parasitol, 42:564 (1956)). Briefly, livers were homogenized in cold HBSS using a Waring Blendor (New Hartford, Ct.). Granulomas were isolated from hepatic parenchymal debris by three to five cycles of serial sedimentation at 1× g in HBSS. Granulomas were suspended at 10% (v/v) in serum-free culture medium RPMI 1640 supplemented with antibiotics and L-glutamine and cultured for 20 to 24h at 37° C. in an atmosphere containing 5% $CO_{2-95}$% air. Cell-free supernatant from the granuloma cultures was retrieved by centrifugation (1000× g 20 min at 4° C.) and filter sterilized (0.22 µm diameter; Millipore Corporation, Bedford, Mass.). The supernatants were stored in aliquots at −20 or −70° C.

In some experiments cell-free supernatants were retrieved by centrifugation (200 g×10 min) and used to purify FsF-1 for immunization of rabbits, or to conduct Western blot analysis. In other experiments, granuloma cells were dissociated by collagenase treatment using methods as described in (Wyler et al., J. Immunol. 132:3142 (1984)). The granuloma cell suspension was first washed with HBSS and then with a solution of phosphate-buffered 0.15M NaCl containing $NaN_3$ (0.015 M) and goat serum (1% v/v; Sigma Chemical Co., St. Louis, Mo.). The washed cells were pelleted and incubated at 4° C. for 0.5 h each in the presence of 10–15 µg/ml of normal rabbit IgG or of rabbit anti-FsF-1 IgG, washed, and then treated with 10 µg/ml goat anti rabbit IgG (H and L chain specific) antibody conjugated with fluorescein isothiocyanate (Fisher Scientific, Pittsburg, Pa.). In some experiments, unstained or the FITC-stained cells were treated with phycoerythrin-conjugated rat anti mouse CD4 antibody (5µ/ml; Becton-Dickinson, Mountain View, Calif.).

Antibody-treated cells were sorted FACStar Plus flow cytometry and analyzed by a FACScan (Becton-Dickinson)

or a Coulter Epics 541 (Coulter Electronics Inc., Hialeah, Fla.) flow cytometer. The fields were gated to exclude autofluorescent and dead cells. The CD4+ sorted cells were washed and suspended (0.6–1.0×10$^6$/ml) in serum-free medium RPMI 1640 supplemented with 0.3 mg/ml bovine serum albumin (BSA; Sigma, St. Louis, Mo.) and incubated for 24h at 30° C. in 5% $CO_2$- 95% air humid atmosphere. Cell-free supernatants were retrieved by centrifugation (200 g×10 min; 4° C.) and analyzed for fibroblast mitogenic activity.

Culture of cells and cell Proliferation assays.

Human diploid fibroblast cultures were established from newborn foreskin as described previously (Wyler et al., *J. Immunol.* 130:1371 (1983)). Primary cultures of bovine aortic endothelial cells (BAEC) were prepared by and were a kind gift of Dr. Michael Gimbrone (Harvard Medical School, Boston, Mass.) (Gimbrone et al., *J. Cell. Biology* 60:673 (1974)). All cells were grown to confluency in 75 cm$^2$ polystyrene tissue culture flasks (Nuncalon, Rochester, N.Y.) in supplemented medium RPMI 1640 containing 10% inactivated FCS (GIBCO Laboratories, Grand Island, N.Y.). When the cultures reached confluency (approximately every 4d), cells were passaged by treatment with 0.2% trypsin-0.1% sodium EDTA (trypsin-EDTA).

For the proliferation assay, cells were suspended in serum-containing supplemented medium at a density of 5 to 6×10$^4$ ml. One ml of the cell suspension was seeded in each well of a 24-well polystyrene tissue culture plate (Nuncalon) and incubated overnight. Cells were then washed twice with warm (37° C.) HBSS and replenished with serum-free medium. On the next day, 100 $\mu$l test samples were added to each well. Twenty hours later, 1 $\mu$Ci [$^3$H]-thymidine (specific activity 6.7 Ci/mM, Dupont-NEN Research Products, Boston, Mass.) was added to each well for 4 h. Cells were then trypsinized and harvested onto glass fiber filters with a cell harvester (Titertek, Flow Laboratories, Rockville, Md.). The magnitude of incorporation of [$^3$H]-thymidine was estimated by scintillation spectrometry.

In selected experiments, cell growth was also assessed by direct quantitation. The cells were cultured as described above. Test samples were added for 96 h, after which the cultures were washed and detached from the monolayer by treatment with trypsin-EDTA. Monodispersed cells were counted in a hemocytometer chamber (Cambridge Instruments, Inc., Buffalo, N.Y.).

Gel filtration chromatography and heparin affinity chromatography.

A 1×40 cm column of Bio-Gel P-30 (Bio-Rad Laboratories, Rockville Center, N.Y.) was equilibrated with PBS (0.15 M) (pH 7.4) and calibrated with the following m.w. markers: blue dextran, OVA,chymotrypsin A., and myoglobin (gel filtration markers; Sigma Chemical Co., St. Louis, Mo.). Approximately 1 ml of unconcentrated crude granuloma culture supernatant was loaded onto the column, which was then run at 4° C. with PBS at a rate of 5 to 6 ml/h. One ml fractions were collected, 0.3 mg/ml BSA (Sigma) was added as a carrier, and the fractions were then dialyzed (Nomincal exclusion, 6 to 8 kDa), first against HBSS, followed by RPMI 1640. The dialyzed material was filter-sterilized before testing in the proliferation assay.

The two or three fractions eluting from the P-30 column with peak fibroblast-stimulating activity (FIG. 1) were pooled and mixed with an equal volume of washed-heparin-Sepharose CL-6B (Pharmacia LKB, Uppsala, Sweden). The mixture was rocked gently over-night at 37° C. in polypro-lylene tubes (Corning, Glassworks, Corning, N.Y.) that had been pretreated by incubation with BSA (1 mg/ml) followed by washing with PBS. The slurry was poured into a column (1×15 cm. Bio-Rad). Material that was not adsorbed (fall-through fraction) was reapplied to the column. The column was then washed extensively with PBS (0.15 M NaCl) and elution was carried out over a 2- to 3-h period with a 30 ml continuous salt gradient (0 to 2.5 M NaCl) and 1-ml fractions were collected. The conductance (ohms$^{-1}$) of each fraction was determined (model CDM, Radiometer, Copenhagen, Denmark). Fractions were dialyzed against medium RPMI 1640 and filter sterilized before testing in the biologic assay.

After determining the concentration of NaCl with which the fibroblast proliferative activity eluted from heparin-Sepharose, a "batch elution" procedure was used for preparing biologically active material from heparin-Sepharose beads. The biologically active fractions prepared by initial gel filtration chromatography were adsorbed to heparin-Sepharose as described above. The tubes were centrifuged (1000× g for 10 min) and the supernatant was recovered and filter-sterilized (0.22-$\mu$m diameter pore). The beads were then washed three times with PBS. After the last wash the beads, suspended in an equal volume of 3.0 M NaCl, were gently mixed at 37° C. for 1 h. The supernatant was removed by centrifugation and dialyzed before testing in the biologic assays. The heparin-Sepharose purified material was designated FsF-1.

FPLC anion exchange chromatography.

The fractions eluting from heparin Sepharose with 1.5 M NaCl were dialyzed (6 to 8 kDa cutoff) at 4° C. against two to three changes of PBS, followed by two changes of 20 mM Tris-HCl, pH 8.0, and applied to a Mono Q column (HR 5/5, Pharmacia, Uppsala, Sweden) that had been equilibrated in the starting buffer (20 mM Tris-HCl, pH 8.0). The fast-performance liquid chromatography apparatus (Pharmacia) was operated at 4° C. Elution was achieved with a gradient of 0 2.2 M NaCl in 20 mM Tris-HCl, pH 8.0, at a flow rate of 1 ml/min. Forty 1 ml fractions were collected. Absorbance (280 nm) and the conductance of each fraction was monitored and 0.3 mg/ml of BSA was added as a carrier protein before each fraction was dialyzed against medium and tested in the proliferation assays.

SDS-PAGE.

Samples were combined with an equal volume of buffer consisting of 10 mM Tris-HCl, pH 6.8, 2% SDS, 5% glycerol, 2% dithiothreitol, and 0.01% bromophenol blue. Samples were analyzed by SDS-PAGE as described by Laemmli (Laemmli et al., *Nature* 227:680 (1970)). Separating gels of 10% acrylamide and stacking gels of 7% were used. Gels were stained with silver nitrate (Morrissey, *Anal. Biochem,* 117:307 (1981)).

Preparation and analysis of anti-FsF-1 antibodies.

Initial (preimmune) serum samples were obtained from two female NZW rabbits (3 to 4 kg, Buckshire Corp., Perkasie, Pa.) which were then immunized with purified FsF-1 by repeated intradermal injections on the back. Ten ml of unfractionated granuloma supernatant (approximately 10 mg of protein by Bradford assay; Bradford Anal. Biochem. 72:248, 1976)) was processed by gel filtration and heparin affinity chromatography (batch elution procedure) as described above. Purified FsF-1 was concentrated to a volume of 1 to 1.5 ml (approximately 1 to 2 $\mu$g; fluorescamine protein assay (Bohlen et al., *Biophys.* 155:213 (1973)) by ultrafiltration using a 6–8 kDa nominal exclusion cellophane dialysis bag suspended in a slurry of polyethylene glycol (molecular mass =8 kDa, Sigma). The concentrate was emulsified in an equal volume of CFA (Sigma).

The rabbits were boosted at 4- to 6-wk intervals by intradermal injections of the same amount of purified FsF-1 in incomplete Freund's adjuvant (IFA) (Sigma). Aliquots of serum obtained routinely 6 to 8 days after each booster injection were stored at either −20 or −70° C. IgG from preimmune or immune serum was prepared by protein -A Sepharose (Sigma) chromatography (Goding, *J. Immunol. Methods* 20:241 (1978)).

The specificity of the anti-FsF-1 antibody was assessed by dot-blot ELISA as described in Hawkes et al., *Anal. Biochem.* 119:142 (1981). Briefly, purified FsF-1 (10 to 15 ng); purified acidic FGF (100 ng, 200 ng); PDGF (40 ng, 100 ng); purified human plasma fibronectin (2, 20, 100 ng (prepared as described in Wyler et al., *J. Immunol.* 138:1581 (1987)); rhIL-2 (2ng, 12 ng, 20 ng; Genzyme, Boston, Mass.); rmIL-3 (2.5 ng, 7.5 ng; Genzyme) rmIL-4 (0.7 ng, 4 ng, 7 ng; Collaborative Research, Bedford, Mass.); rmIL-6 (2.5 ng, 15 ng, 25 ng; Biosource International, Westlake Village, Calif.); rh IL-7 (0.75 ng, 4.5 ng, 7.5 ng; Biosource International); and rm GM-CSF (0.25 ng, 1.5 ng; 2.5 ng; Genzyme), were adsorbed to nitrocellulose paper (Bio-Rad) in a volume of 1 to 5 $\mu$l. The nitrocellulose was then washed overnight in blocking buffer (PBS containing 5% w/v Carnation nonfat powdered milk). The nitrocellulose was then incubated at room temperature for 1 h with anti FsF-1 IgG antibody (1:50 final dilution). After extensive washing with blocking buffer, the nitrocellulose was incubated for 0.5 to 1 h at room temperature in alkaline phosphatase-conjugated goat anti rabbit IgG (Promega Corporation Madison, Wis.). The development of the blot was carried out by incubation with substrate (containing nitroblue tetrazolium chloride and 5-bromo-4 chloro-3imodyl phosphate, p-toluidine salt (Promega)) dissolved in alkaline phosphatase buffer (100 mM Tris-HCl, 100 mM NaCl, 5 mM $MgCl_2$, pH 9.5): 33 ml nitroblue tetrazolium chloride and 16.5 ml 5-bromo-4 chloro-3-imodyl phosphate p-toluidine salt was used for every 5 ml of the buffer. The reaction was stopped with deionized water.

Antibody neutralization of biologic activity.

Purified acidic FGF, PDGF or heparin-Sepharose purified FsF-1 (approximately 10–20 ng in 100 $\mu$l) or culture supernatant of granuloma-derived $CD4^+$ lymphocytes) were combined with preimmune IgG (2.5 $\mu$g in 100 $\mu$l) or anti-rsF-1 rabbit IgG (2.5 $\mu$g in 100 $\mu$l) and the mixture was incubated at 37° C. for 3 to 4 h in polypropylene culture tubes that had been pretreated with BSA. The samples were then filter sterilized and tested in the fibroblast proliferation assay. Alternatively, the samples were incubated with immobilized protein A-Sepharose to remove Ag-antibody complexes; the samples were centrifuged at 1000× g for 10 min and the supernatant was tested for fibrogenic activity.

Amino acid analysis of FsF-1.

Amino acid composition of FsF-1 was determined by analysis of the 1.5 M NaCl eluate from the heparin-Sepharose bound to polyvinylidene difluoride membrane (Millipore Corp., Bedford, Mass. (LeGendre et al., *Biotechniques* 6:154 (1988)). The amino acid composition was determined by the standard method of Waters PICO-TAG.

Reagents. Murine rlL-3, IL-4, and recombinant mouse granulocyte-macrophage CSF were obtained from Genzyme, Boston, Mass. Murine, rlL-6, human rlL-7, human rlL-8 were obtained from Bio-Source International, Westlake Village, Calif. Human PDGF, a-endothelial cell growth factor, goat anti-human PDGF (IgG) were purchased from Collaborative Research. Bovine acidic FGF used for the dot blot ELISA assay and neutralization studies and rabbit antibovine acidic FGF fragment (Leu 60–Leu 98), polyclonal IgG was obtained from UBI, Lake Placid, N.Y.

Biosynthetic labeling of FsF-1

$CD4+$ cells from granulomas were cultured for 24 h in methionine and cysteine- free RPMI 1640 medium (Selectamine®Kit, GIBCO, Grand Island, N.Y.) to which was added 75 $\mu$Ci Tran $^{35}$S-Label® ($^{35}$S *E. coli* hydrolysate labeling reagent containing 70% L-methionine [$^{35}$S] and 15% L-cysteine [$^{35}$S]; sp. act. 1181 Ci/mmole; ICN Biomedical, Irvine, Calif.). The cell-free culture supernatants were collected at 24 h by centrifugation (200 g×10 min) and 200 $\mu$l of the supernatant was first incubated (1–2 hr; 4° C.) with NRIgG (5 or 15 $\mu$g in 200 $\mu$l) and the mixture was then incubated (1 hr; 4° C.) with protein A-Sepharose (50–100 $\mu$l; Sigma). Two hundred microliters of supernatant of this mixture was retrieved following centrifugation (12, 000 g×5 min) and retreated in a similar manner, this time with anti FsF-1 IgG (5 or 15 $\mu$g in 200 $\mu$l) and protein A-Sepharose. The beads were pelleted (12,000 g×5 min), washed twice in phosphate-buffered 0.15 M NaCl and then boiled for 5 min in sample buffer (10 mM Tris-HCl; 2% sodium dodecyl sulfate; 5% glycerol; 2% dithiothreitol; 0.05% pyronin Y; pH 6.8). Supernatant from these treated beads were subjected to electrophoresis in a 70×70×0.5 mm slab gel of 10% acrylamide (BioRad Labs, Richmond, Calif.) using standard method (Laemmli, *Nature* 227:680 (1970)). Following electrophoresis, proteins were transferred electrophoretically (1-2h; 70 volts) onto nitrocellulose paper (BioRad) using standard procedures. The nitrocellulose paper was then exposed to X-ray film (X-OMAT, AR; Kodak, Rochester, N.Y.) for 72 h at −70° C.

RESULTS

Purification of FsF-1.

Figure 1:
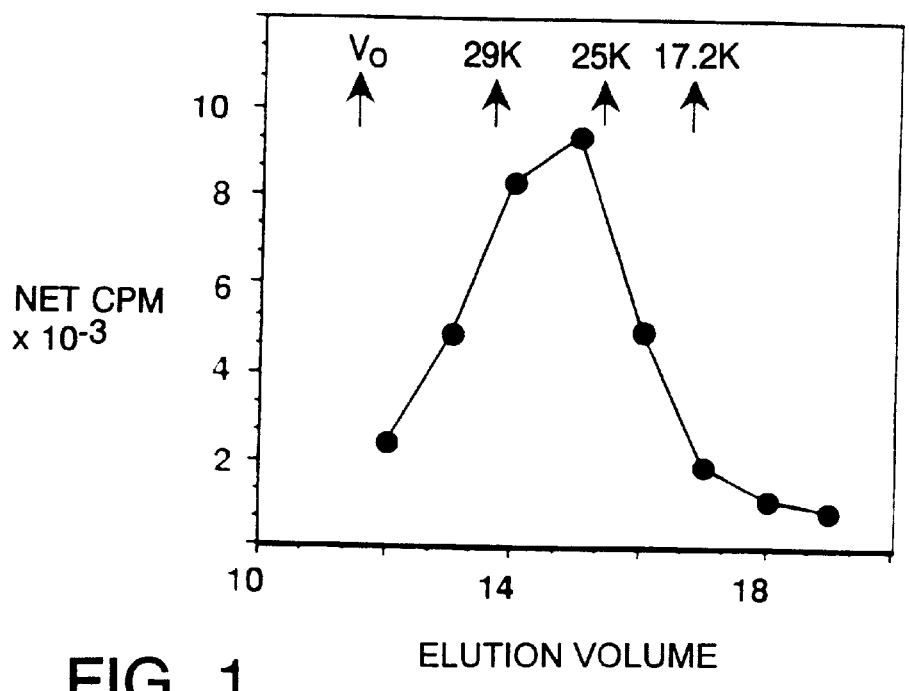

Gel filtration chromatography of granuloma culture supernatant resolves the fibroblast growth factor in fractions with apparent molecular mass 25 to 28 kDa (FIG. 1). Each fraction was tested at different dilutions (from $\frac{1}{10}$ to $\frac{1}{50}$); maximum stimulation of [$^3$H]-thymidine incorporation was obtained with a dilution of $\frac{1}{20}$ of the most active fraction.

Figure 2:
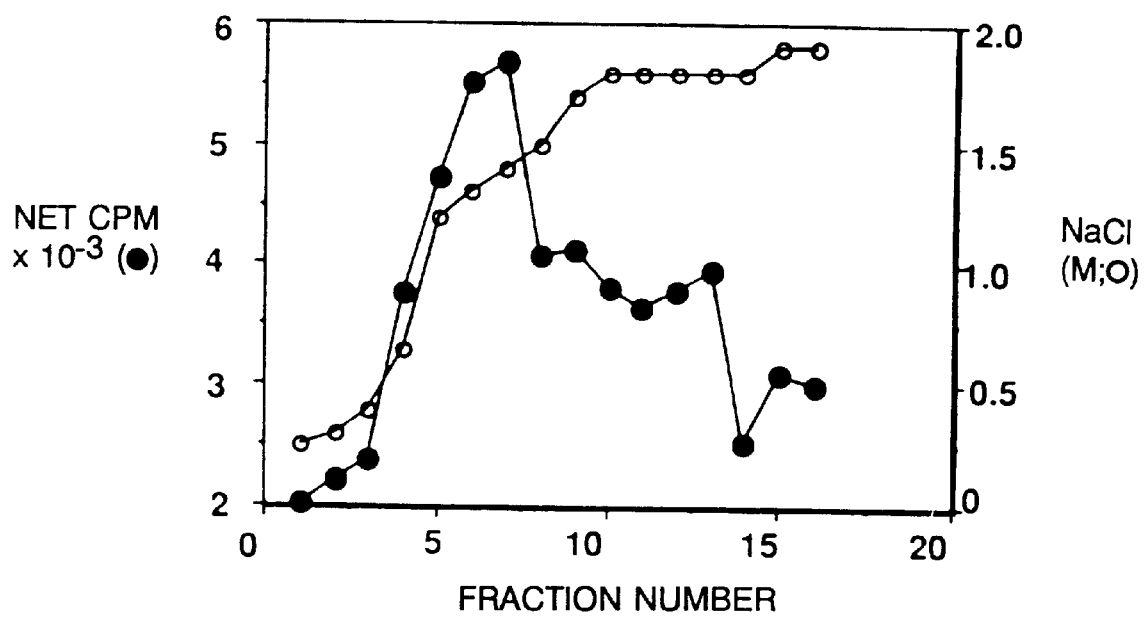

A pool of two or three consecutive active fractions obtained by gel filtration was subjected to heparin-affinity chromatography. When the elution was performed with a linear gradient of NaCl (0.2.5 M), peak mitogenic activity (containing 85 to 90% of the total activity) eluted from the affinity column with 1.25 to 1.5 M NaCl (FIG. 2). Accordingly, we used 1.5 M NaCl to elute the fibroblast mitogen in subsequent experiments. By this procedure, most of the biologic activity was retrieved in the adsorbed fraction; negligible activity was present in the unadsorbed fraction. Maximum fibroblast stimulation was achieved when the active fraction was tested to a dilution of $\frac{1}{100}$ and $\frac{1}{1000}$. Nonspecific binding of the fibroblast mitogen to heparin-free Sepharose 4B beads was not detected in control experiments.

Figure 3:
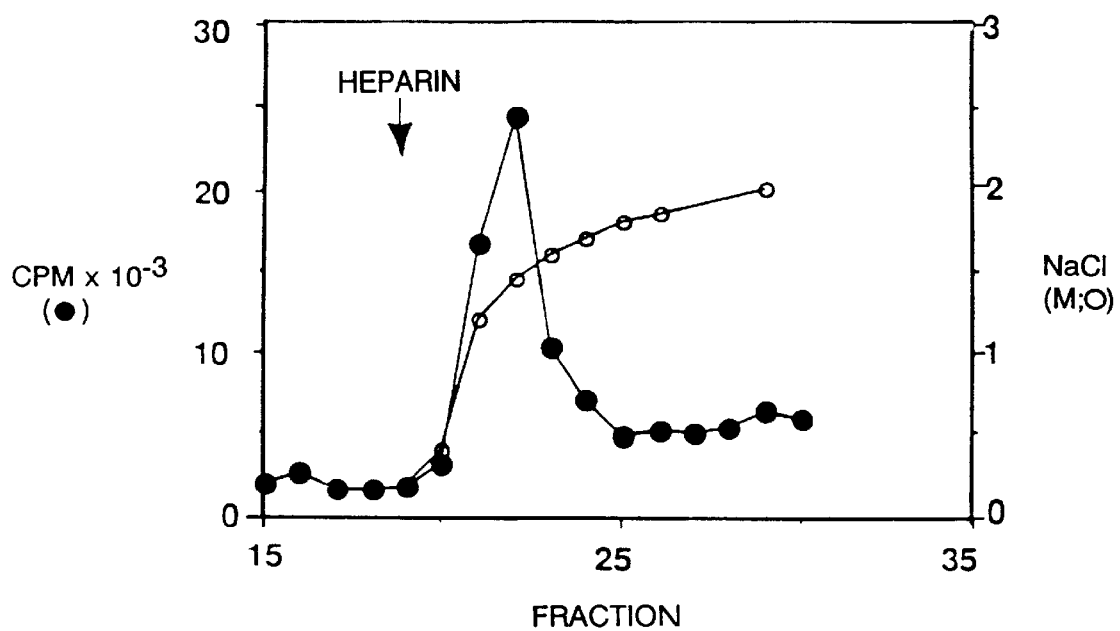

Heparin-Sepharose fractionated material was subjected to anion-exchange FPLC chromatography (FIG. 3). Fibroblast mitogenic activity eluted from the column with 1.2 to 1.5 M NaCl in a single active peak; maximum activity was present in fractions eluting with 1.5 M NaCl. These fractions were active at a concentration of $\frac{1}{100}$ to $\frac{1}{1000}$. Only fractions 17 and 18 detectably adsorbed uv light (280 nm). Commercial heparin (from porcine intestinal mucosa, Sigma, cat. no. H-3125) when applied to a mono Q column under the same conditions also eluted in these two factors.

The biologically active fraction that eluted from heparin-Sepharose was analyzed by silver stain of SDS-PAGE (FIG.

4) and under reducing conditions revealed in single band with molecular mass ≈60 kDa. This band corresponds to the migration position of one of the major proteins detected in electropherograms of crude granuloma supernatant.

Rabbit IgG produced in response to immunization with heparin-purified FsF-1 reacts by dot-blot ELISA with heparin-purified FsF-1 and neutralizes its biological activity. Anti FsF-1 IgG but not pre-immune IgG also identifies in Western blot of crude granuloma supernatant FsF-1 (MW 60 kD), and two of its degredation products (FIG. 5).

Identity of FsF-1.

The heparin affinity of FsF-1, as revealed in the above experiments, suggested that the mitogen might be identical to a previously-defined HBGF. Such factors are classified in part according to their anodic or cathodic migratory behavior during IEF (Lobb et al., *J. Biol. Chem.* 261:1924 (1986)). We established that the granuloma-derived mitogen has $pI^{25}$ 6.2 (Wyler et al., *J. Immunol.* 129:1706 (1982)), thus FsF-1 has a characteristic of class 1 (acidic) HBGF.

We determined the amino acid composition of FsF-1 and compared it with that of bovine acidic FGF. At least 6 of the 15 amino acids analyzed different (by ~50%) in their mole percent content (Table 1). The possibility that the FsF-1 preparation might have been contaminated with heparin places into question the accuracy of the mole-percent determination of serine and glycine (Folkman et al., *Science* 235:442 (1987)). Nonetheless, the extent of the differences in amino acid composition of FsF-1 and FGF indicates their molecular distinctiveness inasmuch as the structure of FGF is highly conserved in evolution (Lobb et al., *Anal. Biochem.* 154:1 (1986)).

We also conducted a series of experiments to assess the potential similarity of FsF-1 to acidic FGF, the prototype class 1 HBGF molecule (Lobb et al., supra). We also compared FsF-1 with PDGF, a group of closely related mesenchymal cell mitogens (LeGendre et al., supra).

Anti-FsF-1 antibody detected FsF-1 in both purified form and in crude granuloma supernatant in a dot-blot ELISA assay (FIG. 6). The antibody did not detect acidic FGF or PDGF, mitogens that were detected with the appropriate homologous antibodies. Furthermore, anti FsF-1 did not detect plasma fibronectin or acidic FGF in a dot-blot ELISA; nor did anti-fibronectin antibody react with FsF-1. Crude granuloma supernatant had no biological activity characteristic of TNF in an L929 cytotoxicity assay and purified TNF was not mitogenic in our assay which utilizes serum-free conditions. We detected no IL-2 activity in granuloma supernatants (Wyler et al., *J. Immunol.* 129:1706 (1982)), and detected no fibroblasts mitogenic activity in rIL-2

Figure 7A:
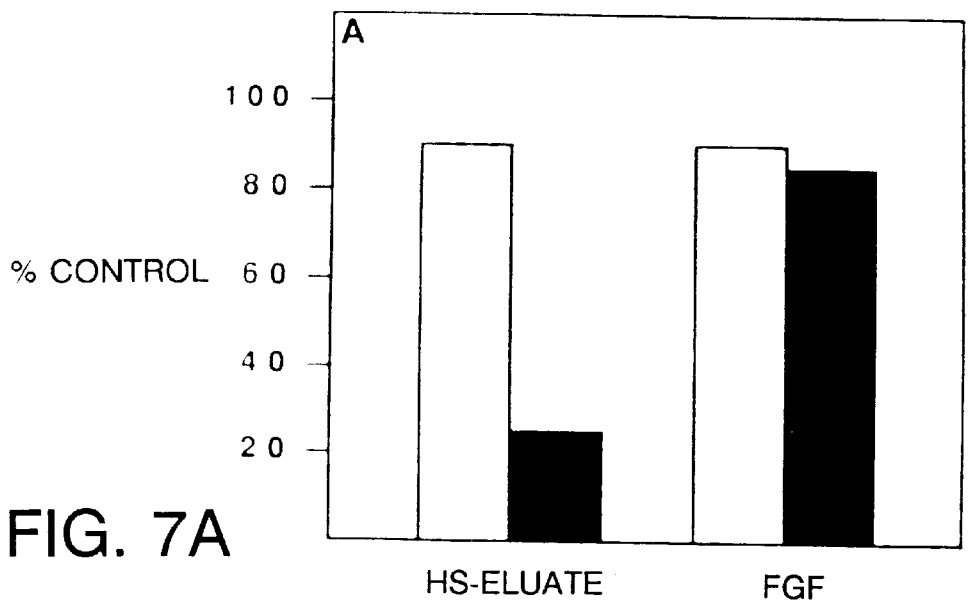
Figure 7B:
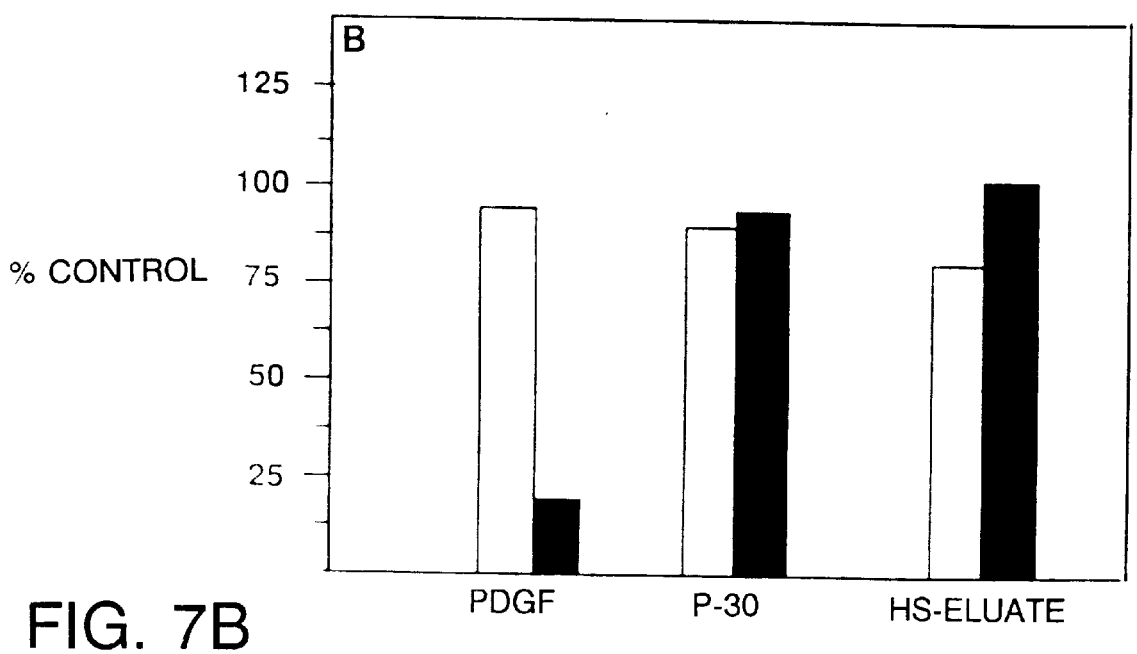

Anti-FsF-1 antibody inhibited the proliferative responses of fibroblasts to FSF-1 (FIG. 7A; p<0.005; comparison by Student's t-test of mean fibroblast responses to FsF-1 in the presence of normal rabbit IgG or anti FsF-1 1 gG in four separate experiments). Under identical conditions, the antibody preparation did not significantly (p>0.4) affect the mitogenic activity of acidic FGF. Furthermore, anti-PDGF, which abrogated the mitogenic effects of PDGF, had no effect on FsF-1 (FIG. 7B).

Figure 8A:
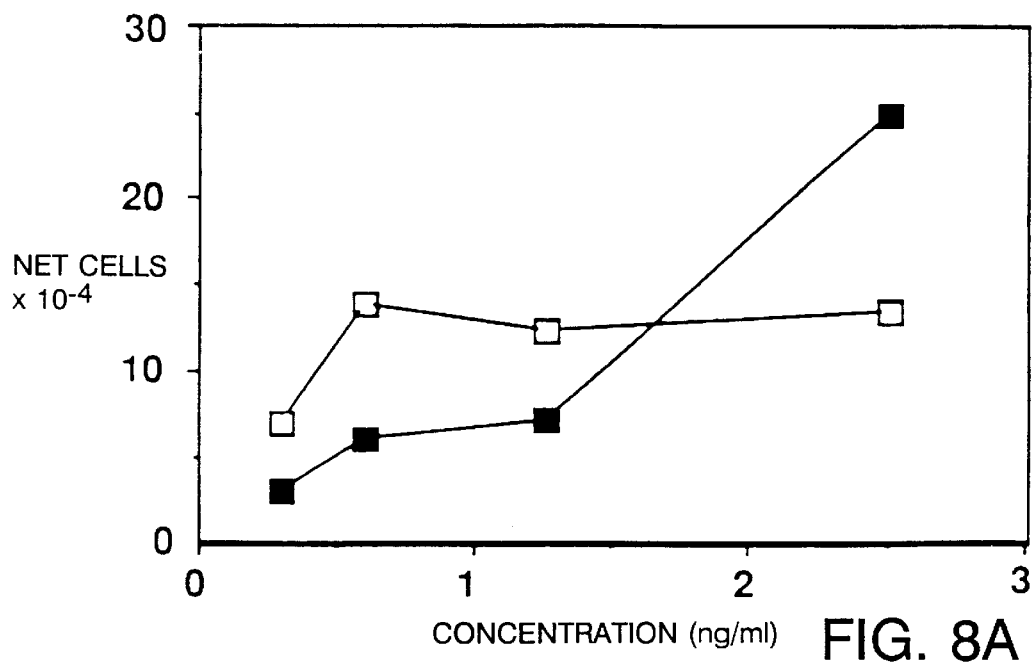
Figure 8B:
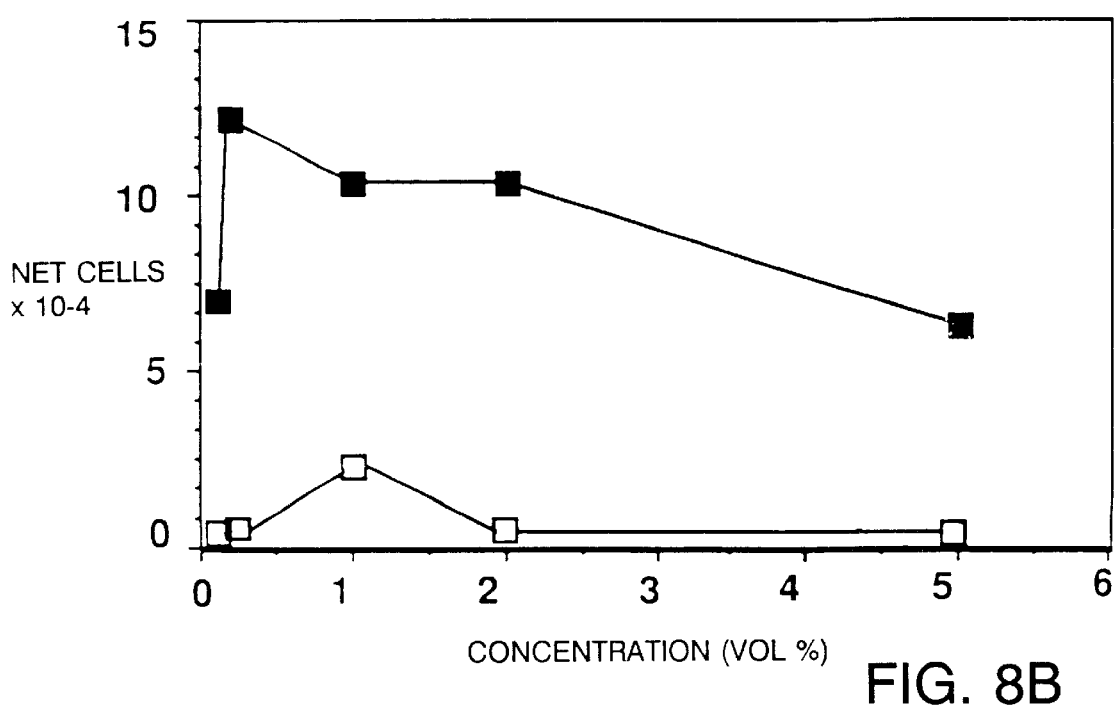

A characteristic feature of class 1 HBGF is their ability to stimulate endothelial cell proliferation (Folkman et al., supra). As shown in FIG. 8A, fibroblasts and endothelial cells proliferate in response to acidic FGF. Inasmuch as the magnitude of the response of endothelial cells to the lower (<2 ng/ml) concentration of acidic FGF is greater than that of fibroblasts, these cells appear to be the more sensitive to this mitogen. In contrast, FsF-1 in concentrations in the range of 1 to 40 ng/ml, did not induce endothelial cell proliferation (FIG. 8B).

Finally, we detected no biological activity in the following commercially-prepared cytokines; rIL-3 (0.2–200 U/ml), rIL-4 (0.05–20U/ml) rhIL-5(1–1000 U/ml), rIL-6 (0.002–1000 U/ml), IL-7 (0.02–100 U/ml) rIL-8 (0.02–100 U/ml) or GM-CSF (0.3–20 U/ml). The lack of relevant biological activity in these cytokines implies that FsF-1 is unique.

Flow cytometry of granuloma cells

Figure 9A:
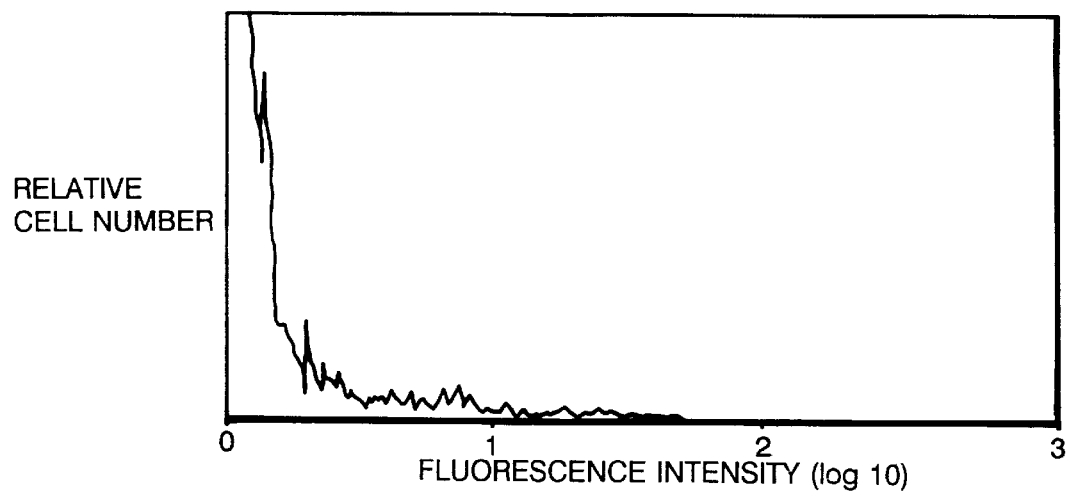
Figure 9B:
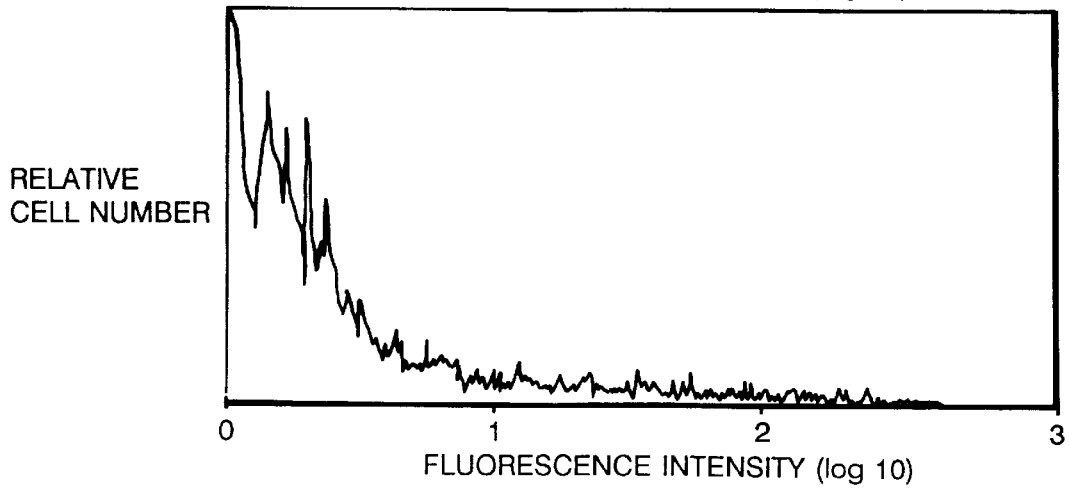
Figure 10A:
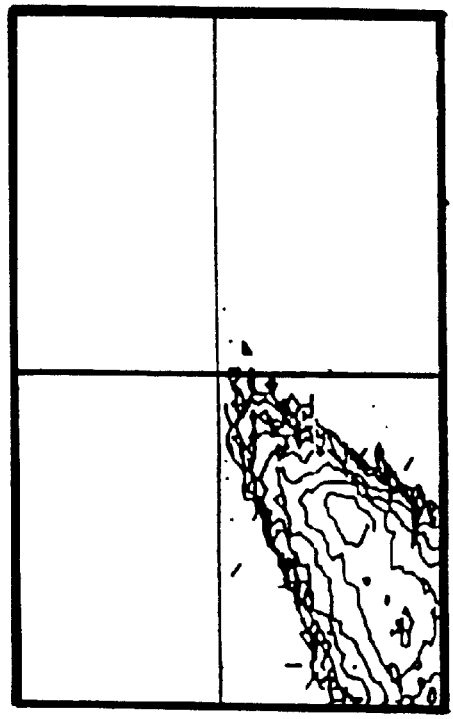
Figure 10B:
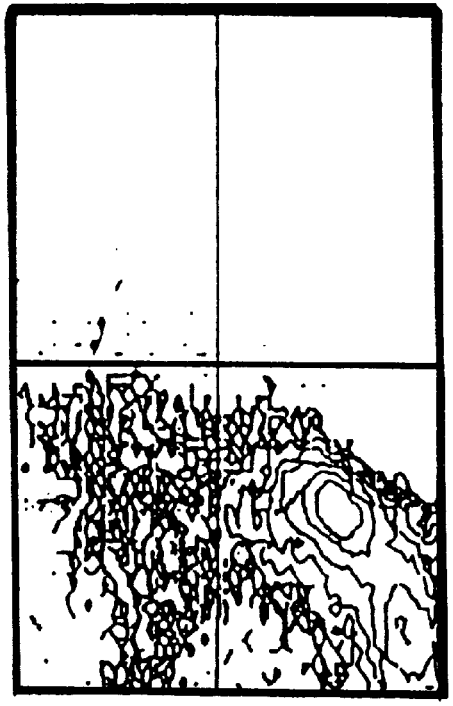
Figure 10C:
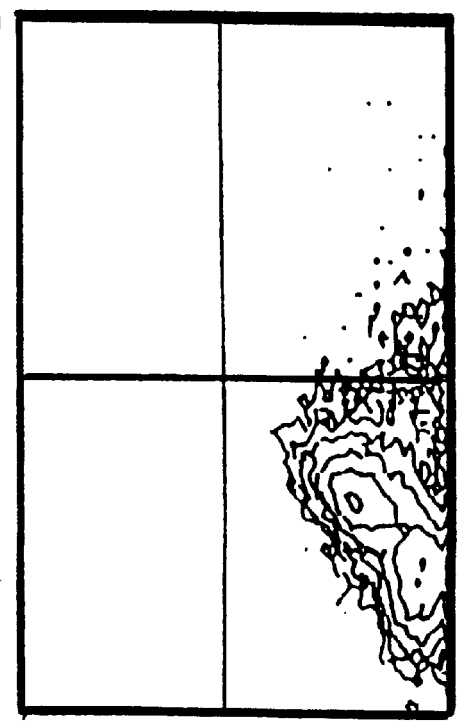
Figure 10D:
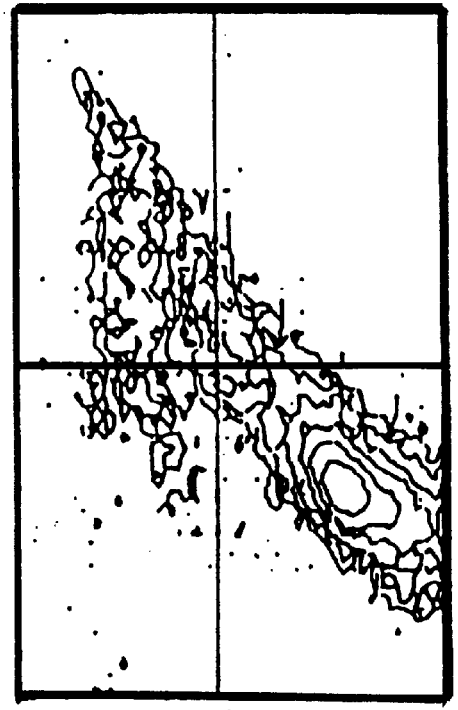

We analyzed granuloma cells by flow cytometry after they were treated with anti FsF-1 IgG (or preimmune IgG) and FITC-conjugated anti IgG with or without subsequent treatment with phycoerythrin-conjugated anti CD4 antibody (FIG. 9 and 10). In the mouse, CD4 is expressed on a subpopulation of lymphocytes but not on macrophages (Crocker et al., *J. Exp. Med.* 166:613 (1987)). Using one-and two-color flow cytometric analysis, we determined that approximately 20–25% of the CD4+ lymphocytes also stained specifically with anti FsF-1.

We next employed FACS to obtain a highly-enriched (99% pure) population of $CD4^+$ granuloma cells that we then incubated at a density of $0.5–1.0 \times 10^6$ cells/ml for 24 h in serum-free medium. The conditioned medium from these cultures stimulated fibroblast proliferation (Table 2). In contrast, culture supernatants of $CD4^+$ lymphocytes isolated from spleen cell suspensions prepared from uninfected mice contained no such biological activity. This indicates that the treatment of cells with anti-CD4 antibody in the course of their purification did not trigger the secretion of FsF-1.

Biosynthetic labeling of FsF-1 in CD4+ lymphocytes

Figure 11:
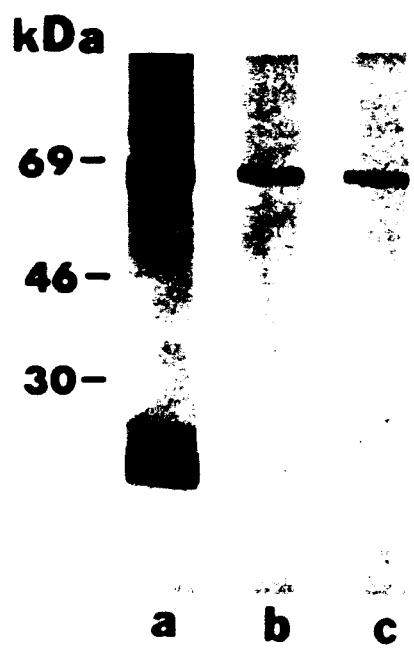

The foregoing results suggested that egg granuloma-derived CD4+ lymphocytes produce FsF-1. To confirm this conclusion more precisely, and exclude the possibility that FsF-1 was merely bound to the CD4+ lymphocytes and subsequently released, we incubated these isolated granuloma cells with $[^{35}S]$-methionine/cysteine for 24 h and processed the culture supernatants by immunoprecipitation with anti FsF-1. Autoradiographs of the electroblots of SDS-PAGE preparations of untreated culture supernatant disclosed in excess of 10–15 distinct bands (FIG. 11). In contrast, immuno-precipitation of the CD4+ lymphocyte supernatant with anti FsF-1 IgG revealed a singled 60 kDa band (FIG. 11). On the basis of its Rf, this band corresponds to the major labelled product of the isolated lymphocytes and to that of heparin-affinity purified FsF-1 from granuloma supernatant (Prakash et al., supra). As noted by Western analysis, preimmune IgG does not react with this protein (FIG. 5).

Heparin affinity chromatography has proven to be a valuable purification procedure in the isolation of certain mesenchymal growth factors and angiogenic factors (Lobb et al., supra). An advantage of this technique is that the relatively high affinity binding of these factors to heparin is uncharacteristic of most proteins (Lobb et al., supra). The simplicity of the scheme we were able to devise for purifying FsF-1 from culture supernatants is a consequence of its heparin-binding property. Early in our studies, we noted that an initial gel filtrations step enhances the efficiency of the subsequent affinity chromatography step, perhaps by removing fibronectin (another heparin-binding protein that is a constituent of these supernatants (Wyler, *Rev. Infect. Dis.* 9(Suppl:5391 (1987)) from the crude granuloma supernatants. The final anion exchange FPLC (FIG. 3) confirmed the homogeneity of biologic activity in the purified fractions, and the single brand (or occasionally a doublet) detected on silver-stained SDS-PAGE gels (FIG. 4) supports the conclusion that purification was achieved. Furthermore, we estimate that the purification scheme resulted in approximately 10,000- to 50,000-fold enrichment in specific activity. We base this estimate on our measurement of the total protein concentration of crude granuloma culture supernatant (~1 mg/ml; Bradford assay (Bradford, *Anal. Biochem.* 72:248 (1976)), our detection of protein in the heparin-Sepharose eluate near the lower limit of sensitivity of the fluorescamine assay (~200 ng/ml (Bohlen et al., supra)), and the dilution of material yielding maximum proliferative responses being 1:10 to 1:20 for crude material and 1:100 for purified material.

The apparent molecular mass ~60 kDa of FsF-1 revealed by SDS-PAGE conflicts with our estimates of molecular mass ~25 to 28 kDa by gel filtration chromatography (FIG. 1). By Western blot analysis of crude granuloma supernatants probed with polyclonal anti FsF-1 antibody, we detected a single band in the range of 55 to 58 kDa and at times also a doublet at 30-kDa band. The basis for this apparent discrepancy in m.w. determination by gel filtration and by SDS-PAGE remains to be elucidated.

However, a number of factors are known to affect migration in gel filtration. In contrast, only the 60 kDa protein was identified by immunoprecipitation of metabolically-labeled $CD4^+$ lymphocyte-derived proteins (FIG. 11). This indicates that the minor bands are apparently products of degradation of FsF-1 most likely generated by granuloma-derived proteases present in culture supernatants (but not in $CD4^+$ lymphocyte culture supernatants). One possibility is that FsF-1 forms aggregates, and that such aggregates formed during heparin-affinity chromatography are resistant to dissociation under the conditions we used in conducting SDS-PAGE.

In addition to providing for a convenient purification method, the fact that FsF-1 is heparin-binding has important implications in establishing its molecular identity. We previously determined that the granuloma-derived mitogen is a protein with pI ≅6.2(7). These properties suggest that FsF-1 might be a member of the acidic heparin-binding growth factor class of proteins (class 1 HBGF), mitogenic proteins of diverse cellular origin that are structurally identical or closely related, and highly conserved between mammalian species (Harper et al., *Biochemistry* 25:4097 (1986)). The class 1 HBGF, exemplified by acidic FGF, are all potent mitogens for fibroblasts as well as endothelial cells. Our indicator endothelial cells from bovine aorta responded in a characteristic manner to bovine FGF but not FsF-1 (FIG. 8). It is unlikely that the lack of response to FsF-1 is due to species differences, because the HBGF are structurally and functionally conserved (Burgess et al., *Annu. Rev. Biochem* 58:575 (1989)), and because we found that another cytokine from egg granulomas with molecular characteristics distinct from FsF-1 could stimulate proliferation of bovine aortic endothelial cells, but not fibroblasts (Wyler et al., *J. Infect. Dis.* 155:728 (1987)). This suggests that FsF-1 probably is distinct from FGF and sensu stricto is not a class 1 HBGF. Supporting this conclusion are our observations that antibodies prepared against FsF-1 neither reacts with FGF in a dot-blot ELISA nor neutralize its biologic activity, whereas it does both to FsF-1 (FIGS. 6 and 7). Finally, the amino acid content of FsF-1 and FGF (acidic and basic) reveal differences indicating that these molecules are not identical (Table 1), and the amino acid sequence of the peptide derived from FsF-1 is distinct from other known proteins.

The antibody preparations permitted us to distinguish FsF-1 from other heparin-binding growth factors (Prakash et al., supra) and to determine by flow cytometry that a subpopulation (20–25%) of CD4+ lymphocytes in granuloma cell suspensions apparently express FsF-1 on their surface (FIGS. 9 and 10). The fact that culture supernatants of CD4+ lymphocytes isolated from egg granulomas contained fibroblast mitogenic activity that was neutralized with anti FsF-1 IgG indicated that these cells secrete the mitogen (Table 2). The definitive evidence that the CD4+ lymphocytes produce and secrete FsF-1 was obtained in experiments involving biosynthetic labelling and immunoprecipitation of CD4+ proteins (FIG. 4). Although the results of the present studies do not exclude the possibility that other granuloma cells also might be potential sources of FsF-1, our prior studies indicate that FsF-1 is not secreted by granuloma macrophages (Wyler et al., supra). Furthermore, since *S. mansoni* egg granulomas from mice treated with anti IL-5 antibodies lack eosinophils (Sher et al., *Proc. Natl. Acad Sci. USA* 87:61 (1990)) but nonetheless secrete fibrogenic activity, eosinophils are an unlikely source of FsF-1. On the other hand, egg granulomas from *S. mansoni*-infected, congenitally athymic mice (which lack mature T lymphocytes and do not develop hepatic fibrosis) produce no fibroblast mitogen (Prakash et al., *J. Immunol.* 144:317 (1990)). This observation is consistent with our conclusion that FsF-1 is a lymphokine.

We conclude that the granuloma CD4+ lymphocytes are stimulated in vivo to produce FsF-1, and that this production is not induced artificially during isolation of the lymphocytes. Several points support this conclusion. First, in contrast to many of the studies that have examined production of fibrogenic proteins by chronic inflammatory cells (lymphocytes and macrophages; for example, see Wahl et al., *J. Immunol* 121:942 (1978); Wahl et al., *Lymphokines* 2:179 (1981), we do not add antigens, mitogens, or other nonspecific stimuli to our granuloma or cell cultures. Second, the cell sorting methods we used did not trigger lymphocytes to produce a fibroblast mitogen (see above). Third, fibroblast mitogenic activity can be detected in extracts of recently isolate egg granulomas (Wyler et al., *J. Infect. Dis.* 144:254 (1981)) and is detectable in the cell-free supernatants of isolated egg granulomas within a few hours of their in vitro incubation (Wyler et al., supra). Fourth, unfractionated splenocytes and splenic CD4+ lymphocytes isolated by flow cytometry fail to spontaneously secrete fibroblast mitogens (Wyler et al., *Infect. Immun.* 38:103 (1982); and the present study). On the other hand, sensitized splenic lymphocytes stimulated with an aqueous extract of schistosomal eggs (concanavalin-binding fraction of soluble egg antigen) do secrete a fibroblast mitogen, presumably FsF-1 (Wyler et al., supra).

It is noteworthy that FsF-1 detected by immunoprecipitation corresponded to a prominent 60 kDa protein produced by isolated granuloma $CD4^+$ lymphocytes (FIG. 5). Our results suggest that FsF-1 might be a major protein produced by this subpopulation of granuloma cells. We have observed that sensitized splenic lymphocytes from *S. mansoni*-infected mice, when stimulated with an aqueous extract of schistosoma eggs secrete a fibroblast mitogen, presumably FsF-1, Wyler et al., *Infect. Immun.* 38:103 (1982). It therefore seems likely that $CD4^+$ cells are stimulated in vivo to produce FsF-1 in response to egg antigens. Based on our current observation, such production may continue at least briefly when the lymphocytes are dissociated from the eggs and antigen-presenting cells. The notable finding that FsF-1 not only is secreted but also can remain associated with the surface of $CD4^+$ lymphocytes suggests that in addition to the action of the secreted cytokine, direct contact between membrane-associated FsF-1 positive lymphocytes and fibroblasts might stimulate fibroblast growth.

A number of cytokines (IL-1, TNF, TGFB), some of which were originally identified on the basis of the other biological activities they possess, also have been shown to exhibit fibrogenic activity in vitro (for example, see Schmidt et al., *J. Immunol.* 128:2177 (1982); Vilcek et al., *J. Exp. Med.* 163:632 (1986); Sugarman et al., *Science* 230:943 (1985); Massague, *J. Biol. Chem.* 260:7059 (1984); Leof et al., *Proc. Natl. Acad. Sci. USA.* 83:2453 (1986)). In addition, fibroblast growth factors, some of which were purified from other sources and were recognized for this biological property (PDGF [Ross et al., *Cell* 46:155 (1986)], FGF [Gospodarowicz et al., *J. Biol. Chem.* 250:2515 (1975); Gospodarowicz et al., *J. Biol.* 253:3736 (1978)]), and heparin-binding epidermal growth factor [HB-EGF;Higashiyama et al., *Science* 251:936 (1991)]) have been found to be produced by macrophages. However, based on its biochemical composition, physicochemical properties, and antigenicity, FSF-1 is distinct from these fibroblast growth factors. Moreover, the fact that FsF-1 is a lymphokine is an additional distinguishing characteristic. Indeed, because we have not detected fibroblast mitogenic activity in several purified and recombinant lymphokines, and since avid heparin-binding is not a known characteristic of most lymphokines, we believe that FsF-1 is a previously unidentified lymphokine.

Detection of FsF-1 in granuloma supernatants and serum of mice infected with *S. mansoni*

Figure 12:
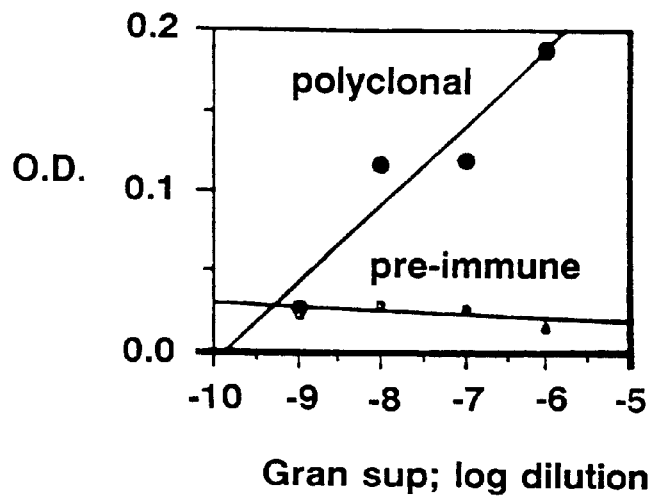
FIG. 12 is a line graph depicting the results of an ELISA antigen-capture assay of FsF-1 in granuloma supernatants.

FsF-1 can be detected in highly-dilute granuloma supernatant in an antigen-capture ELISA (Nourel, et al. (1994) Am. J. Trop. Med. Hyg. 50:585–594). Wells of ELISA plates were coated with one of the Mabs shown above (approximately 100 ng/well). After blocking with gelatin, crude granuloma supernatants (that contain approximately 4 µg/ml FsF-1) were added at the dilutions shown. After removing the unbound material, the captured FsF-1 was detected with monospecific, polyclonal rabbit anti FsF-1 IgG followed by alkaline phosphatase-conjugated goat anti rabbit IgG. Pre-immune rabbit IgG did not detect the captured FsF-1. The readings were blanked against O.D. of wells in which buffer instead of granuloma supernatant was added. The assay apparently is sensitive to at least pg/ml concentrations, consistent with expectations based on similar antigen-capture assays for other lymphokines. (FIG. 12).

An antigen-capture ELISA was also used to detect FsF-1 in sera of unifected C57BL/6 mice or mice infected with Schistosoma mansoni for 8 or 20 weeks. Sera from two sets of mice were compared simultaneously in the same assay. A rat anti-murine FsF-1 monoclonal antibody (IgG) bound to Nunculon plates (which were then blocked with a gelatin-containing blocking buffer) was used to capture FsF-1 in sera diluted 1:100. After washing the plates with blocking buffer, rabbit IgG anti-murine FsF-1 (diluted 1:200) was added. After incubation and washing, a goat anti-rabbit IgG conjugated with alkaline phosphatase was added. After washing, the substrate was added and the optical density read in an ELISA reader. These readings were blanked against wells in which the reagents from all steps of the assay were included with the exception of the mouse serum. A control assay which was also conducted simultaneously, was identical in all respects to the experimental assays but for the exclusion of the monospecific rabbit anti FsF-1 detector.

Figure 13:
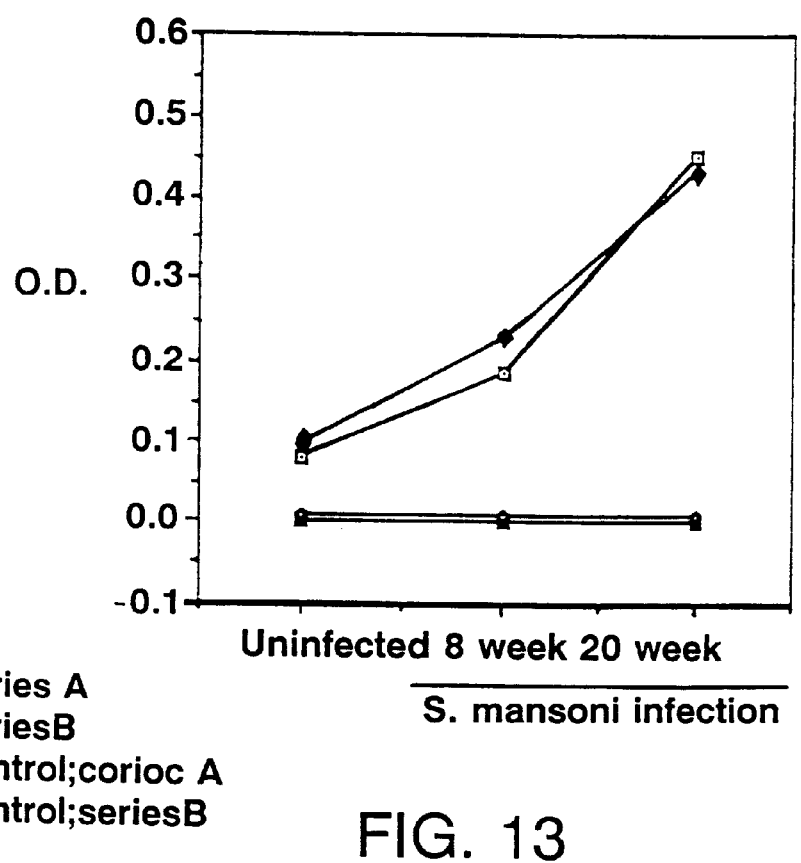
FIG. 13 is a line graph which depicts the levels of FsF-1 in sera of uninfected or infected mice in an ELISA assay.

The results of this assay (FIG. 13) indicate that normal mouse serum contains very little, if any, detectable FsF-1, but sera from infected mice contain elevated levels that continue to rise during mid chronic stage. The control assays performed further confirm the specificity of the assay; the FsF-1 levels observed are not due to either the reaction of the rabbit anti FsF-1 IgG with the monoclonal antibody, or the reaction of the captured antigen with the goat anti-rabbit IgG.

CLONING AND ANALYSIS OF MURINE cDNA

Our efforts to obtain amino acid sequence data from the purified FsF-1 polypeptide (also designated fibrosin) were hindered by the fact that FsF-1 is blocked to Edman degradation and is also strikingly resistant to enzymatic proteolysis. Accordingly, as an alternative approach to establish its molecular identify, we sought to clone FsF-1 by heterologous expression of a CD4$^+$ lymphocyte-derived cDNA library in COS-7 cells.

Several CD4$^+$ lymphocyte clones and cell lines (provided as gifts from D. C. Parker, University of Oregon, Portland, Ore., and L. Glimcher, Harvard School of Public Health, Boston, Mass.) were screened for their ability to secrete fibroblast mitogenic activity into culture supernatants following in vitro stimulation. Cells were propagated in supplemented medium RPMI 1640 containing 10% FBS. Cells at mid-log growth were washed extensively in HBSS and $10^6$ cells were cultured in 1 ml serum-free medium supplemented with 0.3 mg/ml BSA and 10 µg/ml concanavalin A (Con A; Sigma Chemical Co.,St. Louis, Mo.) for 24 h at 37° C. in a humidified atmosphere of 5% $CO_2$-95% air. Cell-free supernatants were retrieved by centrifugation (200 g×10 min) and stored at −20° C. until tested in a fibroblast proliferation assay. Five of the 30 cell lines tested were positive in the fibroblast proliferation assay, and a CDC25 cell line (CD4$^+$Th2 lymphocyte line; Tony et al., *J. Exp. Med.* 162:1695–1708, 1986) was selected for further analysis. This cell line was propagated biweekly as described (Tony et al., supra) and used 2–3 weeks later for preparation of culture supernatants.

Antibody neutralization of fibrogenic activity

Specific polyclonal IgG was prepared by immunizing rabbits with highly purified murine FsF-1, as previously described. This antibody preparation did not react (by dot blot ELISA) with a variety of recombinant murine lymphokines. IgG purified from pooled sera of rabbits prior to immunization (NRIgG), and which did not react with FsF-1, served as a control. Cell-free supernatants (undiluted) from lymphocytes or transfected COS-7 cells were incubated with IgG (final concentration, 2.5 to 7.5 µg/100 µl) at 37° C. for 2–3h in polypropylene culture tubes (Falcon #2063; Becton-Dickinson Labware, Lincoln Park, N.J.) that had been previously treated with BSA (1 mg/ml) and washed, to reduce non-specific adsorption of proteins. Immune complexes were removed from selected mixtures with protein A coupled to Sepharose beads (Sigma). Following incubation for 1 h at 37° C., the beads were removed by centrifugation (100 g×10 min.) The samples were then filter-sterilized (0.22µm diameter pore size; Millipore Corp., Bedford, Mass.) and tested in a fibroblast proliferation assay.

cDNA library and expression cloning

A murine CDNA library prepared from mRNA isolated from ConA-stimulated cells of the CDC25 line was obtained from DNAX Research Institute of Molecular and Cellular Biology, Palo Alto, Calif. The library was constructed in the vector pcDSRα296 which contains a unique promoter that permits high-level, transient expression of the CDNA insert in COS-7 cells (Takebe et al., *Mol. Cell Bio.* 8:466–472, 1988). Like the parental pcD vector originally designed by Okayama and Berg (supra), pcDRα296 allows a high level of expression of full-length cDNA inserts under the control of the simian virus 40 (SV40) early promoter. SV40-derived DNA fragments are arrayed in these vectors to permit transcription, splicing, and polyadenylation of the cloned cDNA. A DNA fragment containing both the SV40 early region promoter and two introns normally used to splice the virus 16s and 19s late mRNAs is placed upstream of the cDNA cloning site to ensure transcription and splicing of the cDNA transcripts. This DNA fragment can promote two alternate kinds of splicing. Most often (60–70% of transcripts) splicing occurs at the 16s RNA intron junction and places the cDNA initiator ATG codon first in line from the 5' end of the mRNA. When splicing occurs at the 19s RNA intron, it retains an ATG codon upstream of the cDNA in the processed mRNA. Therefore, if the clone contains an incomplete cDNA, translation from the upstream ATG codon may yield a fusion protein.

E. coli transformants containing the pcDSRα296 vectors were expanded in L-broth medium containing ampicillin (50μg/ml) and plasmids were isolated on Qiagen columns (Qiagen Inc., Chatsworth, Calif.). For transfection, $5 \times 10^5$ COS-7 cells (Okayama et al. Meth. Enzym. 154:3–28, 1987) were seeded on 60 mm tissue culture dishes (Falcon) in supplemented Dulbecco's modified Eagle's medium (DMEM; GIBCO) containing 10% FBS (GIBCO). Cells were grown overnight to a density visually estimated to be 60–70% confluency. Cells were then washed with serum-free DMEM buffered with 50 mM Tris (pH 7.4). and plasmid DNA (1–5 μg) in serum-free medium (4 ml per plate) was added, followed by the addition of DEAE dextran (200 μg/ml; Pharmacia, Piscataway, N.J.). After co-incubation with plasmid DNA for 4–5h, COS-7 cells were washed and treated for 2–3h with 100 μM chloroquine (Sigma) in the presence of 2% FBS. Cells were then washed and grown overnight in DMEM with 4% FBS. The following day, cells were washed and replenished with DMEM containing 0.3mg/ml BSA. Forty-eight to seventy-two hours later, culture supernatants were collected and tested for their ability to stimulate fibroblast proliferation.

For controls, COS-7 cells were transfected with the pcDSRα296 plasmid containing a murine IL-4 cDNA insert (DNAX), and were subsequently maintained under the above conditions except that the cells were cultured in 2% FBS. Supernatants of these cultures were harvested after 48 to 72 hours and tested for IL-4 activity on an indicator cell line (HT-2; Rennick et al. J. Immunol. 134:910–914, 1985) and in the fibroblast proliferation assay.

DNA nucleotide sequence analysis

Nucleotide sequences on both positive and negative CDNA strands were determined by the dideoxy-chain termination protocol with supercoiled DNA templates (Sanger et al., Proc. Natl. Acad. Sci. USA 74:5463–5467, 1977). Areas which were rich with G-C rich were sequenced by PCR using a cycle sequencing kit from Epicentre Technologies. The nucleotide sequence was compared by FASTA and BLAST programs to sequences archived in GenBank.

Peptide synthesis

A 71 amino acid residue oligopeptide (MW 7620, as confirmed by mass spectrometry) with sequence corresponding to that of the cDNA (amino acid arginine at position 26 to leucine at position 96, FIG. 18; SEQ ID NO.: 1) was synthesized by the methods of t-boc NMP chemistry using Perkin-Elmer Applied Biosystems 430A Peptide Synthesizer (Clark-Lewis, Science 231:134–139, 1986). The peptide was purified by HPLC using Vydac CA column and eluted in a single fraction with trifluoroacetic acid/acetonitrile gradient.

RESULTS

CDC25 lymphocyte line produces fibroblast mitogen

Of the 30 lymphocyte lines and T-cell hybridomas we tested, five elaborated detectable fibroblast mitogenic activity in culture supernatants following in vitro stimulation with ConA for 24h. ConA had no intrinsic fibroblast mitogenic activity in our fibroblast assay. We chose line CDC25, a Th2 line for which a cDNA library was available for further analysis. Culture supernatants of CDC25 cells stimulated fibroblast [$^3$H]-thymidine incorporation in a concentration-dependent manner; peak responses were detected at a concentration of 10% (the maximum tested; FIG. 14A). Anti FsF-1 IgG reduced the activity of the CDC25 culture supernatant by 21% and 47% with 2.5 μg/100μl and 5 μg/μg IgG respectively (FIG. 14B), relative to responses in the presence of the same concentrations of pre-immune IgG (NRIgG) which we previously established does not significantly alter the fibroblast responses to purified FsF-1. Furthermore, in Western blot anti FsF-1 IgG recognizes a single protein band (apparent Mw 50–60 kD) in CDC25 culture supernatants subjected to SDS-PAGE; NRIgG does not recognize this protein.

CDC25 library contains cDNA that encodes a fibroblast growth factor

Culture supernatants of COS-7 cells transfected with the entire CDC25 library (containing approximately $10^6$ clones) stimulated fibroblast [$^3$H]-thymidine incorporation in a concentration-dependent manner (FIG. 15). Because culture supernatants from IL-4 cDNA transfectants (which contained 200–250 U/ml IL-4 based on results in the HT-2 proliferation assay) had minimal effects on fibroblast proliferation, we concluded that the CDC25 library contained cDNA that specifically encoded a fibroblast mitogen that is not IL-4. We used sib-selection as a strategy to clone this cDNA (Yokota et al., Proc. Natl. Acad. Sci. USA 82:68–72, 1985; Lee et al. Proc. Natl. Acad. Sci. USA 83:2061–2065, 1986).

The CDC25 library was partitioned into pools of $10^3$ clones that were seeded into separate wells of microtiter plates containing L-broth and ampicillin. Pools, estimated to contain $10^4$ clones, were prepared by combining wells within a row. COS-7 cells were transfected with plasmid DNA prepared from these pools and the transfectant culture supernatants (tested at various concentrations, to a maximum of 10%) were assayed for their ability to enhance fibroblast [$^3$H]-thymidine uptake at least 2–3 fold above background (positive transfectant).

Of the 20 pools initially prepared and tested, 3 (15%) were positive. One of the three pools (pool B) was selected because the biological activity in the supernatant of pool B transfectants could be neutralized with anti FSF-1 IgG. Pool B was subdivided into 8 separate pools (each containing approximately $10^3$clones) and plasmid DNA prepared from each pool was used to transfect COS-7 cells. Conditioned medium from four of the transfectants (50%) had significant mitogenic activity. Based on antibody neutralization of bioactivity, one of the pools (2B) was selected. Pool 2B was then subdivided into 16 pools, each estimated to contain 100 clones. Five of the pools (31%) produced positive transfectants. Two of the positive pools were plated on solid agar, and ten colonies were screened; 8 of these colonies produced positive transfectants.

One of the clones (2B3) was subcloned twice on solid agar and analyzed in detail. The supernatant of 2B3 transfectant was active in a fibroblast growth assay over a wide concentration range; the log-linear dose-response relationship was biphasic (FIG. 16A). AntiFsF-1 IgG virtually abolished the fibrogenic activity of 2B3 transfectant supernatant (FIG. 16B). Notably, with each round of sib selection, the potency of the positive transfectant culture supernatants (dilution producing maximum fibroblast stimulation) increased (FIG. 17). The potency increased approximately 2000-fold from transfection with the whole library to transfection with 2B3 clone.

Nucleotide sequence of clone 2B3

Clone 2B3 contains a cDNA insert of 216 bp and a single open reading frame (ORF) starting with arginine (nucleotide position 76–79; FIG. 18; SEQ ID NO.: 1) and terminating with leucine (nucleotide position 289–291) followed by the stop codon TAA. Thus, the ORF codes 71 amino acids and is followed by 11 untranslated codons that precede the poly(A) tail. Since this ORF does not contain an internal initiating ATG, polypeptide synthesis is initiated at the first in-phase ATG codon present in the vector's 16s splice junction area, 72 base pairs upstream from the 5' end of the insert, and the total open reading frame of 288 nucleotides encodes a fusion protein. No significant homology of this sequence with sequences archived in GenBank could be identified.

Analysis of the deduced amino acid sequence (FIG. 18; SEQ ID NO.: 1)) indicates that the $NH_2$ terminal 15 to 20 deduced amino acid residues of the fusion protein are hydrophobic, and therefore predicted to serve as a secretion signal sequence (Perlman et al., J. Mol. Biol. 167:391–409). If it does serve this function it would be expected that cleavage occurs following the alanine residue at position 15 or 20 of the fusion protein, resulting in a mature peptide containing either 81 or 76 amino acids (predicted MW 9–10 kD.) Alternative cleavage sites might exist. Since gel filtration chromatography of the transfectant culture supernatants displays fibroblast mitogenic activity in fractions with MW 30 kD, the protein is also modified in vivo by glycosylation.

Fibroblast growth stimulation by synthetic peptide

A 71 mer peptide which was synthesized from the deduced amino acid sequence of 2B3 stimulated fibroblast proliferation (based on cell counting) in a concentration-dependent manner (FIG. 19). Notably, in 12 separate assays (6 in which cells were assayed after 72h incubation and 6 after 96 h incubation), peak mitogenic activity was observed with peptide concentrations between $10^{-13}$ and $10^{-11}$ M; additional activity was detected at concentrations in the $10^{-6}$ M range. The dose-response pattern we observed is reminiscent of our experience with crude and purified natural FsF-1 as well as with supernatants of the 2B3 transfectant (FIGS. 16A-B).

CLONING OF FULL-LENGTH MURINE AND HUMAN CDNA

Preparation and analysis of murine T-cell hybridomas that produce FsF-1/fibrosin We prepared and cloned T-hybridoma cells that secrete FsF-1 upon Con A stimulation because this relatively homogeneous source: (1) provides a "renewable" in vitro source from which we can purify natural FsF-1; (2) provided mRNA from which full length fibrosin cDNA could be prepared for analysis and heterologous expression; and, (3) allows standardization of in situ hybridization methods to detect fibrosin mRNA, and in the future can be used to study regulation of fibrosin gene expression.

Individual (cloned) FsF-1+ lymphocytes were selected by FACS (using rabbit anti FsF-1 IgG and FITC-goat anti rabbit IgG as described previously) from a population of splenocytes obtained from a mouse with 8 week S. mansoni infection and stimulated overnight with Con A. Individual cells were fused with thymoma BW 5147 cells using standard methods (Coligan et al., eds., Current Protocols in Immunology, Vol. 1, John Wiley & Sons, Inc., pp. 3.14.1–3.14.11 (1994)). We selected hybridomas that on stimulation with Con A (in the absence of serum) produced fibroblast mitogenic activity, and confirmed by ELISA, neutralization, and immunopurification that this biological activity derived from FsF-1 in the supernatants. Positive hybridomas were subcloned 2–3 times by limiting dilution. Cloned hybridoma cells were adapted to growth in GIBCO SFM (serum-free medium) to avoid serum contamination of culture supernatants. Representative results are shown in FIG. 20.

Analysis of these T cell hybridomas indicate T hybridomas produce fibroblast mitogenic activity (FIG. 20). Second, the hybridoma-derived mitogen is heparin-binding and elutes with high NaCl concentration (two characteristic properties of granuloma-derived FsF-1) (FIG. 21): the non-binding fraction (fall-through) had no activity, and the 1.0 and 1.5 M NaCl eluate contained only 60 KD protein (SDS-PAGE) that was detected by Western blot using anti-FsF-1 antibodies. Third, SEA (10 µg/ml; fraction that lacks direct mitogenic activity) stimulates hybridoma # B12 production of FsF-1. Response to various concentrations of cell culture supernatant are shown relative to CPM in fibroblasts grown in medium alone in FIG. 22. Fourth, Western blot analysis of crude hybridoma supernatant using anti FsF-1 Mabs (D6, GI, Al) that had been prepared to granuloma-derived FsF-1 identified a 60 kD band in the same manner that they identified FsF-1 in crude granuloma culture supernatants. (FIG. 23) (Lane 1, hybridoma supernatant; lane 2, granuloma supernatant). Noteworthy is that the Mabs do not react with albumin (ELISA) and partially neutralize bioactivity.

In addition, crude culture supernatant from Con A-stimulated T hybridoma (B12) was incubated with Mab IgG (#111A5/D8 5 µg/ml) and immune complexes were precipitated with Sepharose-conjugated mouse-anti-rat kappa Mab. Beads were retrieved by centrifugation, washed with PBS (pH 7.2), placed in Centricon-100 filtration units and treated with 0.5 M Na acetate (pH 4.3), then subjected to ultrafiltration of the proteins≦100 kD. The filtrate was neutralized with Tris buffer and tested in the bioassay. The control was identical treatment of T-hybridoma supernatant, but excluding incubation with anti FsF-1 Mab. Bioactivity was compared with heparin-purified T-hybridoma-derived mitogen. Medium control is CPM in fibroblast cultured with medium alone. (FIG. 24). These results indicate that a Mab against FsF-1 immunopurified the mitogenic activity produced by the con A stimulated T cell hybridoma B12. Taken together, these data provide the strong evidence that T-hybridomas produce the same FsF-1 that we previously purified from granuloma supernatants.

Cloning of full-length fibrosin cDNAs from mouse T-cell hybridoma cells and human peripheral blood lymphocytes.

We first established (by RT PCR) that Con A-stimulated murine T-hybridoma cells express 2B3 mRNA and confirmed this conclusion by in situ hybridization of Con A-activated T-T hybridoma cells using a 194 bp ds 2B3-derived oligonucleotide probe having the sequence:

```
                                                  (SEQ ID NO.: 4)
C-TCA-CTA-AGC-CAG-AGG-CCA-AAG-TGC-CCC-CCT-CCC-TTT-

CGC-CTA-CCA-CCC-AAG-TTC-TCA-TGC-CCT-CCG-AGG-GCT-

GAG-GAA-GGA-GGA-ACT-AAA-GGA-ATA-GGG-GTT-TCA-TGT-

ACA-TAT-TTA-TCA-CCC-CTT-CCA-CAA-ATC-CCC-CAG-ACC-

TTT-TGT-ACA-TTT-TTA-CAG-GGG-TGC-CCC-TCC-CTA-TAA-

TTC-CCT-TCC-TGG-T.
```

Next, we designed four gene-specific DNA oligomers based on the 2B3 nucleotide sequence; we used them for additional (confirmatory) RT PCR, and subsequently also for PCR cloning. The four PCR primers are named T1, B3, B2, and B1 (the "T" stands for top strand sequence and the "B" stands for bottom strand sequence; the order of T1, B3, B2, and B1 reflects their order in 2B3 as oriented from 5' end to 3' end of the top strand).

```
                                                  (SEQ ID NO.: 5)
T1:  C-TCA-CTA-AGC-CAG-AGG-CCA-AAG-TG (SEQ ID NO.: 6)
B1:  A-CCA-GGA-AGG-GAA-TTA-TAG-GGA-GG (SEQ ID NO.: 7)
B2:  CC-TTT-AGT-TCC-TCC-TTC-CTC-AGC-C (SEQ ID NO.: 8)
B3:  CA-TGA-GAA-CTT-GGG-TGG-TAG-GCG-A
```

With three pairs of PCR primers (T1/B3, T1/B2, and T1/B1) and total RNA prepared from mouse T-hybridoma cells, we obtained RT PCR products with the expected sizes of 60 bp, 93 bp, and 194 bp, respectively. When we examined total RNA prepared from PHA-stimulated human peripheral blood mononuclear cells (PBMC) with these primer pairs, we obtained only one RT PCR product of 60 bp.

To clone the 5' segment of fibrosin cDNA, we first tried two PCR cloning methods, "RACE PCR" (Frohman, in PCR Protocol. A guide to methods and applications, p. 28–38. Academic Press, NY 1990) and "RACE NO MORE PCR" (Weis, *Nucleic Acid Res.* 22:3427–3428, 1994) with the three specific PCR primers B1, B2, and B3. The human (PBMC) and murine (T-hybridoma) RNAs were used to prepare total cDNAs as templates. Because the RACE NO MORE was successful with mouse cDNA, we pursued this method. RACE NO MORE method is based on the rare event of 5' end PCR priming in a linear PCR with only one reverse primer annealed to a random hexamer primed cDNA whose 5' end sequence is unknown. A subsequent second PCR with the first primer and a second reverse primer located 5' end to the first primer specifically amplifys the 5' end unknown region plus a stretch of known sequence at the 3' end. From the mouse source, we obtained in the second PCR a 470 bp product with primer pair B2/B1, which followed the first PCR that was carried out with the B1 primer. When primer pair B3/B1 was used in the second PCR, we obtained a 435 bp product, as expected. Both 470 bp and 435 bp products were loaded on separate gels, and after electrophoresis the bands were excised and purified (Wang and Rossman, *Nucleic Acid Res.* 22:2862–2863, 1994). Confirmatory experiments provided the expected results. Specifically, by regular PCR, the purified 470 bp yielded a 93 bp product with primer pair T1/B2, and a 60 bp product with primer pair T1/B3. The 435 bp product yielded only the 60 bp product.

The 470 bp and 435 bp products were then cloned into CR3 vector of Invitrogen's Eukaryotic TA Cloning Kit following the manufacturer's protocol. DNA sequencing of several resulting plasmid clones of each product revealed that the 470 bp and 435 bp products all contained the expected portions of mouse 2B3 sequence at the 3' end. The 5' end was composed of the B1 sequence, followed by a 9 bp portion of the 2B3 segment (an artifact—not unexpected—created by this new PCR approach), which in turn was followed downstream by a new 311 bp sequence adjacent to the complete 2B3 sequence. These sequences indicated that both the 470 bp and the 435 bp products were derived from a common RACE NO MORE PCR event. Notably, the 311 bp sequence contained three in-frame ATG triplets; the first one was located at bp 76, the second 15 bp downstream from the first. The sequences surrounding the first and the second ATGs conform with Kozak's criteria for translation initiation (Kozak, *J. Cell Biol.* 108:229–241, 1989).

The full length mouse cDNA has a total length of 571 bp with a 75 bp untranslated leader sequence and encodes a polypeptide chain of about 149 residues (including 78 encoded by the upstream 311 bp sequence and 71 encoded by 2B3) (FIG. 25; SEQ ID NO.: 2).

To confirm that the new 311 bp mouse sequence created by RACE NO MORE was not an abberation of the method, and to obtain the complete apparently full-length fibrosin cDNAs from both mouse and human sources, we designed two PCR primers. Primer T2 is a 28-mer forward primer derived from the mouse sequence in the 5' end untranslated leader sequence, upstream from the first ATG; primer B4 is a 35-mer reverse primer, derived from the mouse 2B3 sequence at its 3' end untranslated region, including 10 A's of its poly-A tail of more than 50 A's.

```
                                                  (SEQ ID NO.: 9)
T2: AAG-CCA-GGG-TTG-GAA-GGC-AAA-GGT-CAC-A (SEQ ID NO.: 10)
B4: TTT-TTT-TTT-TCC-AGT-CTG-AGG-ATT-TAA-TTA-ACC-AG
```

Using these primers, we obtained a 524 bp PCR product from the cDNA prepared using total RNA from the mouse T-cell hybridoma, and a 500 bp PCR product from the cDNA prepared using total RNA from human PBMC.

Both PCR products were gel purified, and then used as templates in separate PCRs with a panel of seven pairs of mouse primers: T2/B1, T2/B2, T2/B3, T1/B1, T1/B2, T1/B3, and T1/B4. The mouse 524 bp PCR product generated seven bands of the expected sizes, and the human 500 bp PCR product yielded six bands of the expected sized.

DNA sequencing of both PCR products have demonstrated that human (FIG. 26; SEQ ID NO.: 3) and mouse (FIG. 25; SEQ ID NO.: 2) fibrosin cDNAs are comprised of two portions: (1) the 311 bp segment in the 5' region; and, (2) the 2B3 segment in the 3' region. Sequence analysis indicates that there are considerable interspecies differences in the 5' portion of fibrosin cDNA, including some sequence deletions. On the other hand, the 2B3 segment is conserved. The conservation of the 2B3 segment is not surprising since this contains the biologically-active domain that can stimulate growth of both murine and human fibroblasts in vitro.

EXPRESSION OF FsF-1 POLYPEPTIDE

Polypeptides according to the invention can be produced by expression from a recombinant nucleic acid having a sequence encoding part or all of an FsF-1 polypeptide of the invention, using any appropriate expression system: e.g., transformation of a suitable host cell (either prokaryotic or eukaryotic) with the recombinant nucleic acid in a suitable expression vector. The precise host cell used is not critical to the invention. The method of transfection and the choice of expression vector will depend on the host system selected. Mammalian cell transfection methods are described, e.g., in Ausubel et al. (*Current Protocols in Molecular Biology*, supra); expression vectors may be chosen from those discussed, e.g., in *Cloning Vectors: A Laboratory Manual* (P. H. Pouwels et al., Supp. 1987). Stably transfected cells can be produced by integration of FsF-1 DNA into host cell chromosomes.

DNA sequences encoding the polypeptides of the invention can also be expressed in a prokaryotic host cell. DNA encoding an FsF-1 polypeptide of the invention or a fragment thereof is carried on a vector operably linked to control signals capable of effecting expression in the prokaryotic host. If desired, the coding sequence can contain, at its 5' end, a sequence encoding any of the known signal sequences capable of effecting secretion of the expressed protein into the periplasmic space of the host cell, thereby facilitating recovery of the protein and subsequent purification. Prokaryotes most frequently used are various strains *E. coli;* however, other microbial can also be used. Plasmid vectors are used which contain replication origins, selectable markers, and control sequences derived from a species compatible with the microbial host. Commonly used prokaryotic control sequences (also referred to as "regulatory elements") are defined herein to include promoters for transcription initiation, optionally with an operator, along with ribosome binding site sequences.

USE

Using the methods described herein, overexpression of the nucleic acids of the invention can be used to isolate large quantities of FsF-1 polypeptides that are capable of efficiently stimulating fibroblast growth, proliferation and chemotaxis. Alternatively, the methods described herein can be used to generate synthetic or recombinant polypeptides that are capable of inhibiting one or more of the biological activities of the naturally occurring FsF-1 polypeptide. For example, such antagonistic peptides can be produced and tested in any of the assays described herein for the ability to neutralize the mitogenic and/or chemotactic activity of the naturally occurring polypeptide.

In one application, the FsF-1 polypeptides of the invention will be admixed with a pharmaceutically acceptable carrier substance, e.g., physiological saline, and administered to a mammal, e.g., a human, suffering from a wound or a burn. The particular mode of administration is preferably topical. The dosage of polypeptide will vary, depending on such factors as the type and severity of the lesion, but will generally be at a dosage sufficient to stimulate adequate fibroblast proliferation and chemotaxis to the lesion site. A typical dosage range would be 1 ng to 10 mg of the polypeptide, and treatment can be repeated as deemed necessary to promote healing.

In another application, the antibodies of the invention which have been characterized, according to the methods described herein, as being capable of neutralizing the activity of an FsF-1 polypeptide will be used to treat disorders in which the reduction of FsF-1 levels are desirable, e.g., chronic inflammatory diseases. In one example, the antibodies of the invention can be conjugated to any immunotoxin well known to those skilled in the art, and used to target FsF-1 producing cells. These antibodies will be formulated in a pharmaceutically acceptable carrier substance and administered, e.g., intravenously, intramuscularly, orally, parenterally, transdermally, or topically. The particular mode will depend upon the condition being treated and the general status of the animal, and will be apparent to those skilled in the art. The dosage of the antibody will also vary, depending on such factors as the type and severity of the disease, but will generally be at a dosage sufficient to inhibit the formation of a serious fibrotic conditions. A typical dosage range would be 1 ng to 10 mg of the antibody per kg body weight, and can be repeated weekly or daily as deemed necessary.

The nucleic acids of the invention can also be used therapeutically. Oligonucleotides which are antisense to FsF-1 mRNA (or nucleic acid constructs which express RNA that is antisense to FsF-1 mRNA) can be utilized as an antifibrotic therapy. The method would involve introduction of the antisense oligonucleotide into lymphocytes in vivo. The antisense hybridizes with endogenous FsF-1 mRNA, interfering with translation of the protein, thereby reducing production of the polypeptide. Methods of antisense design and introduction into host cells are described, for example, in Weinberg et al., U.S. Pat. No. 4,740,463.

OTHER EMBODIMENTS

Other embodiments are within the following claims.

For example, the invention includes any protein which is substantially homologous to murine or human FsF-1 as well as other naturally occurring FsF-1 polypeptides. Also included are: allelic variations; natural mutants; induced mutants; chimeric polypeptides that include a FsF-1 polypeptide; proteins encoded by DNA that hybridizes under high stringency conditions (e.g., see *Current Protocols in Molecular Biology*, supra to a naturally occurring nucleic acid encoding FsF-1; and polypeptides or proteins specifically bound by antisera to FsF-1, especially by antisera specific to the 2B3 fragment of FsF-1.

The invention also includes biologically active polypeptide fragments or analogs of the recombinantly produced FsF-1 of the invention. By "biologically active" is meant possessing any in vivo or in vitro activity which is characteristic of the FsF-1 of the invention as assayed by the methods described herein. A polypeptide fragment possessing at least 40%, more preferably at least 70%, and most preferably at least 90% of the activity of the FsF-1 polypeptide described herein. As used herein, the term "fragment", as applied to a polypeptide, will ordinarily be at least about 20 contiguous amino acids, and preferably at least 40 contiguous amino acids in length. Polypeptide fragments can be generated by methods known to those skilled in the art, and the biological activity of a FsF-1 fragment can be assessed by methods known to those skilled in the art.

Preferred analogs of the invention include FsF-1 polypeptides (or biologically active fragments thereof) whose sequences differ from the naturally occurring FsF-1 polypeptide by amino acid sequence differences or by modifications that do not affect sequence, or by both. Analogs of the invention will generally exhibit at least 70%, preferably at least 80%, more preferably at least 90%, and most preferably at least 95% or even 99%, homology with all or part of a naturally occurring FsF-1 polypeptide. The length of comparison sequences will generally be at least 20 amino acids residues, and preferably, more than 40 amino acid residues. Differences in amino acid sequence can be by conservative amino acid substitutions, for example substitution of one amino acid for another of the same class (e.g., valine for glycine, arginine for lysine, etc.) or by one or more nonconservative amino acid substitutions, deletions, or insertions which do not destroy the analog's biological activity as measured by the assays described herein. Modifications include in vivo or in vitro chemical derivatization of polypeptides, e.g., acetylation or carboxylation. Also included are modifications of glycosylation, e.g., those made by modifying the glycosylation patterns of a polypeptide during its synthesis and processing or in further processing steps, e.g., by exposing the polypeptide to glycosylating enzymes from cells that normally provide such processing, e.g., mammalian glycosylation enzymes. Also embraced are versions of the same primary amino acid sequence that have phosphorylated amino acid residues, e.g., phosphotyrosine, phosphoserine, or phosphothreonine; and analogs that include residues other than naturally occurring L-amino acids, e.g., D-amino acids or non-naturally occurring or synthetic amino acids, e.g., β or γ amino acids. Preferred analogs also include FsF-1 (or biologically active fragments thereof) which are modified for the purpose of increasing peptide stability, e.g., one or more desaturated peptide bonds, or non-peptide bonds. Alternatively, increased stability can be conferred by cyclizing the peptide molecule.

While preferred embodiments have been illustrated and described, it is understood that the present invention is capable of variation and modification and, therefore, should not be limited to the precise details set forth, but should include such changes and alterations that fall within the purview of the following claims.

TABLE 1

Comparison of the amino composition of heparin-purified FSF-1 (two separate preparations) and bovine acidic FGF

| Amino Acid | Mol percent[a] | | |
|---|---|---|---|
| | FSF-1 | FSF-1 | FGF* |
| Asp and Asn | 2.93 | 1.85 | 9.63 |
| Glu and Gln | 14.22 | 9.85 | 11.00 |
| Ser | 12.31 | 14.33 | 6.88 |
| Gly | 22.87 | 24.16 | 9.70 |
| His | 0.08 | 0.26 | 3.4 |
| Arg | 5.05 | 3.97 | 4.13 |
| Thr | 6.15 | 6.23 | 6.18 |
| Ala | 8.85 | 7.62 | 3.4 |
| Pro | 5.89 | 5.46 | 4.82 |

TABLE 1-continued

Comparison of the amino composition of heparin-purified FSF-1 (two separate preparations) and bovine acidic FGF

| Amino Acid | Mol percent[a] | | |
|---|---|---|---|
| | FSF-1 | FSF-1 | FGF* |
| Tyr | 2.08 | 3.58 | 4.8 |
| Val | 5.46 | 5.94 | 3.4 |
| Met | 0.72 | 1.85 | 0.68 |
| Ile | 3.75 | 4.02 | 4.13 |
| Leu | 7.55 | 7.69 | 13.06 |
| Phe | 1.96 | 2.5 | 4.82 |
| Lys | 0.13 | 0.72 | 8.94 |

[a] Mol percent = $\frac{\text{mole of amino acid}}{\text{mole of total protein}} \times 100\%$.

TABLE 2

Fibroblast proliferative response ($^3$H-thymidine incorporation) to culture supermatants of CD4+ lymphocytes isolated from schistosomal egg granulomas.

| Additive to fibroblast culture | $^3$H-thymidine incorporation (CPM)[1] |
|---|---|
| Medium alone | 5282 ± 822 |
| FBS, 10% | 40,765 ± 6099 |
| granuloma CD4+ cells | |
| 1:5[2] | 10,411 ± 411 |
| 1:15 | 7305 ± 36 |
| 1:50 | 6330 ± 356 |
| spleen CD4+ cells | |
| 1:5 | 5063 ± 852 |

[1] Mean ± SEM of triplicate determinations in representative experiment of three performed.
[2] Final dilution of CD4+ cell supernatant tested in fibroblast cultures

---

We claim:

1. A substantially pure polypeptide consisting of the amino acid sequence of SEQ ID NO:11 from amino acid 26 to amino acid 96.

2. The substantially pure polypeptide of claim 1, wherein the polypeptide is at least 75% pure by weight.

3. The substantially pure polypeptide of claim 1, wherein the polypeptide is at least 90% pure by weight.

4. The substantially pure polypeptide of claim of claim 1, wherein the polypeptide is at least 99% pure by weight.

* * * * *